(12) United States Patent
Gentsler

(10) Patent No.: US 7,141,044 B2
(45) Date of Patent: Nov. 28, 2006

(54) ALTERNATE SITE GENE THERAPY

(75) Inventor: Curtis C. Gentsler, Snohomish, WA (US)

(73) Assignee: EKOS Corporation, Bothwell, WA (US)

( * ) Notice: Subject to any disclaimer, the term of this patent is extended or adjusted under 35 U.S.C. 154(b) by 476 days.

(21) Appl. No.: 10/317,255

(22) Filed: Dec. 11, 2002

(65) Prior Publication Data

US 2004/0002677 A1 Jan. 1, 2004

Related U.S. Application Data

(60) Provisional application No. 60/340,745, filed on Dec. 11, 2001.

(51) Int. Cl.
*A61M 31/00* (2006.01)
(52) U.S. Cl. .................................... 604/500; 604/21
(58) Field of Classification Search .......... 604/20–22, 604/500, 506–509, 522, 93.01, 96.01, 101.01, 604/101.03, 101.05, 103.01, 103.02, 103.08, 604/264, 523; 623/1.41–1.48, 23.64; 424/422–423; 601/2
See application file for complete search history.

(56) References Cited

U.S. PATENT DOCUMENTS

| | | |
|---|---|---|
| 4,821,740 A | 4/1989 | Tachibana et al. |
| 4,953,565 A | 9/1990 | Tachibana et al. |
| 5,007,438 A | 4/1991 | Tachibana et al. |
| 5,081,993 A | 1/1992 | Kitney |
| 5,158,071 A | 10/1992 | Umemura et al. |
| 5,197,946 A | 3/1993 | Tachibana |
| 5,269,291 A | 12/1993 | Carter |
| 5,318,014 A | 6/1994 | Carter |
| 5,328,470 A | 7/1994 | Nabel et al. |
| 5,362,309 A | 11/1994 | Carter |
| 5,368,036 A | 11/1994 | Tanaka et al. |
| 5,380,273 A | 1/1995 | Dubrul et al. |
| 5,415,636 A | 5/1995 | Forman |
| 5,431,663 A | 7/1995 | Carter |
| 5,474,531 A | 12/1995 | Carter |
| 5,558,642 A | 9/1996 | Schweich et al. |
| 5,569,198 A | 10/1996 | Racchini |
| 5,609,574 A | 3/1997 | Kaplan et al. |
| 5,628,728 A | 5/1997 | Tachibana et al. |
| 5,630,837 A | 5/1997 | Crowley |
| 5,713,848 A | 2/1998 | Durbrul et al. |
| 5,735,811 A | 4/1998 | Brisken |
| 5,779,673 A | 7/1998 | Roth et al. |

(Continued)

FOREIGN PATENT DOCUMENTS

JP H02-180275 7/1990

(Continued)

OTHER PUBLICATIONS

Akhtar, *Anti-HIV therapy with antisense oligonucleotides and ribozymes: realistic approaches or expensive myths?* (J. Antimicrob Chemother. 38(2): 159-165, 1996).

(Continued)

*Primary Examiner*—Catherine S. Williams
(74) *Attorney, Agent, or Firm*—Knobbe, Martens, Olson & Bear LLP

(57) ABSTRACT

A method is described for performing gene therapy at an alternate site when it is undesirable or impossible to perform gene therapy at the injured or diseased region. A gene therapy composition is administered using a catheter adapted to deliver ultrasound to facilitate uptake of the gene therapy composition into one or more cells at the alternate site. The treated section may then be transplanted to another region of the body which is diseased or injured.

9 Claims, 26 Drawing Sheets

U.S. PATENT DOCUMENTS

| | | |
|---|---|---|
| 5,836,896 A | 11/1998 | Rosenschein |
| 5,846,218 A | 12/1998 | Brisken et al. |
| 5,876,989 A | 3/1999 | Berg et al. |
| 5,895,356 A | 4/1999 | Andrus |
| 5,916,192 A | 6/1999 | Nita et al. |
| 5,922,687 A | 7/1999 | Mann et al. |
| 5,938,595 A | 8/1999 | Glass et al. |
| 5,941,868 A | 8/1999 | Kaplan et al. |
| 5,997,497 A | 12/1999 | Nita et al. |
| 6,001,069 A | 12/1999 | Tachibana et al. |
| 6,024,718 A | 2/2000 | Chen et al. |
| 6,096,000 A | 8/2000 | Tachibana et al. |
| RE36,939 E | 10/2000 | Tachibana et al. |
| 6,135,976 A * | 10/2000 | Tachibana et al. ............ 604/21 |
| 6,176,842 B1 | 1/2001 | Tachibana et al. |
| 6,210,356 B1 | 4/2001 | Anderson et al. |
| 6,228,046 B1 | 5/2001 | Briskin |
| 6,287,271 B1 | 9/2001 | Dubrul et al. |
| 6,296,619 B1 | 10/2001 | Brisken et al. |
| 6,346,098 B1 | 2/2002 | Yock et al. |
| 6,372,498 B1 | 4/2002 | Newman et al. |
| 6,425,853 B1 | 7/2002 | Edwards |
| 6,461,296 B1 | 10/2002 | Desai |
| 6,652,581 B1 | 11/2003 | Ding |
| 6,680,301 B1 | 1/2004 | Berg et al. |
| 6,794,369 B1 | 9/2004 | Newman et al. |
| 6,929,633 B1 | 8/2005 | Evans et al. |
| 2002/0032394 A1 | 3/2002 | Brisken et al. |
| 2002/0068717 A1 | 6/2002 | Borreiil |
| 2003/0069525 A1 | 4/2003 | Brisken et al. |
| 2004/0039329 A1 | 2/2004 | Ueberle |
| 2004/0106841 A1 | 6/2004 | Shaw et al. |
| 2005/0027247 A1 | 2/2005 | Carrison et al. |

FOREIGN PATENT DOCUMENTS

| | | |
|---|---|---|
| WO | WO 96/07432 | 3/1996 |
| WO | WO 97/19645 | 8/1997 |
| WO | WO 99/25385 | 5/1999 |
| WO | WO 99/33500 | 7/1999 |
| WO | WO 99/34858 | 7/1999 |
| WO | WO 99/39738 | 8/1999 |

OTHER PUBLICATIONS

Anderson, *Human gene therapy*. (Nature 392:25-30, 1998).
Branch, *A Good Antisense Molecule is Hard to Find*, (Trends in Biochem Sci 23: 45-50, 1998).
Crooke, *Basic Principles of Antisense Therapeutics* (Springer-Verlag, Eds, New York, 1998, pp. 1 and 4).
Ho and Parkinson, *Antisense Oligonucleotides as Therapeutics for Malignant Diseases*, (Seminars in Drug Discovery 24(2): 187-202, 1997).
Orkin and Motulsky, *Report and Recommendations of the Panel to Assess the NIH Investment in Research on Gene Therapy*, (p. 1-38, Dec. 7, 1995).
Romano et al., *Latest Developments in Gene Transfer Technology: Achievements, Perspectives, and Controversies over Therapeutic Applications*, (Stem Cells 18: 19-39, 2000).
Somia and Verma, *Gene Therapy: Trials and Tribulations*, (Nature Reviews Genetics 1: 91-99, 2000).
Verma et al., *Gene Therapy—promises, problems and prospects*, (Nature 389: 239-242, 1997).

* cited by examiner

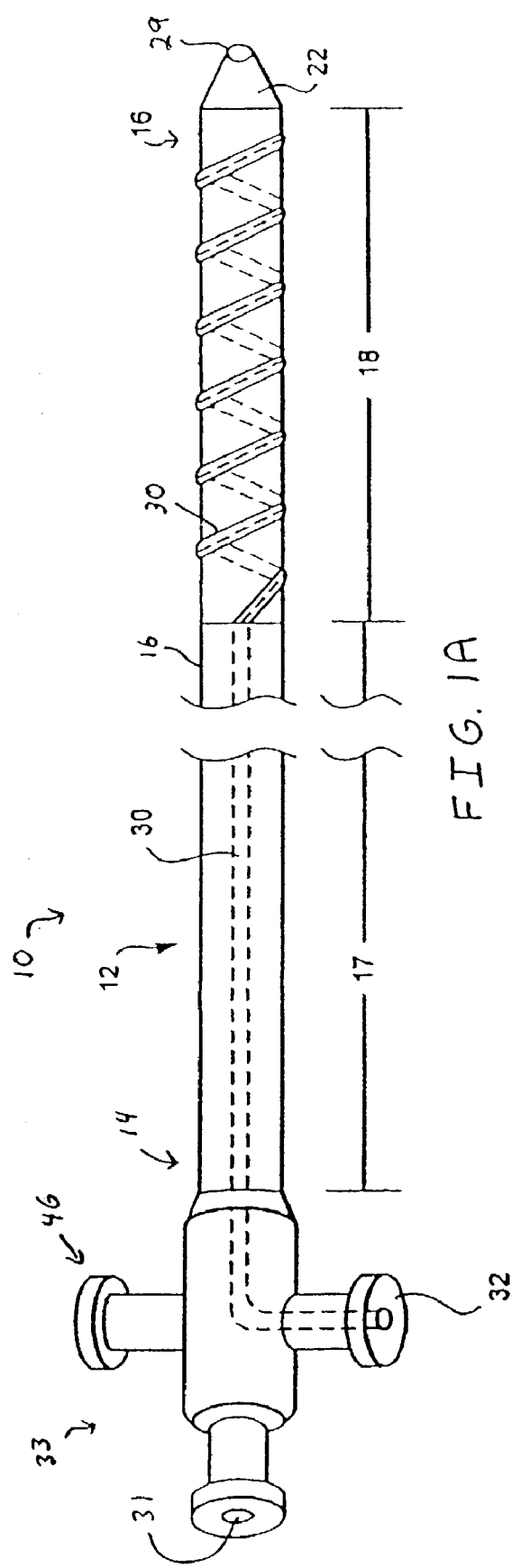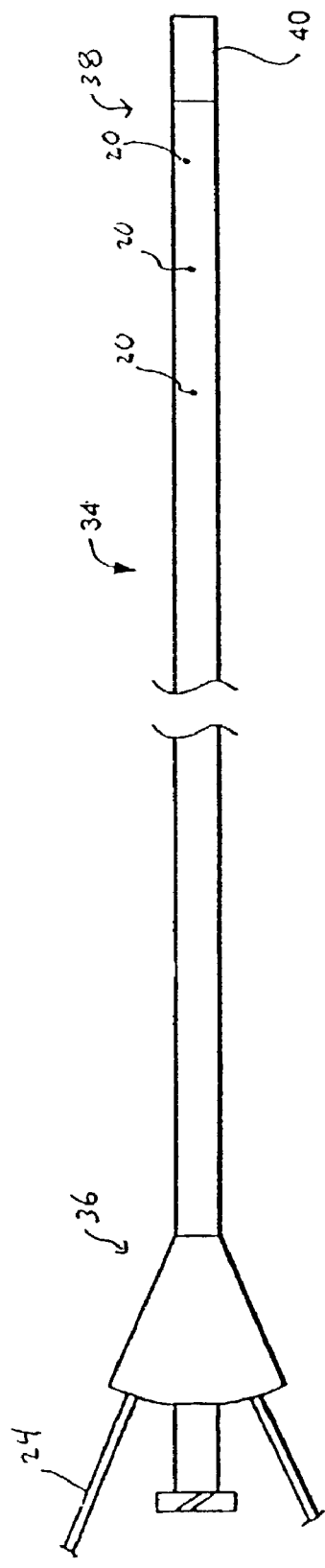
FIG. 1A
FIG. 1B

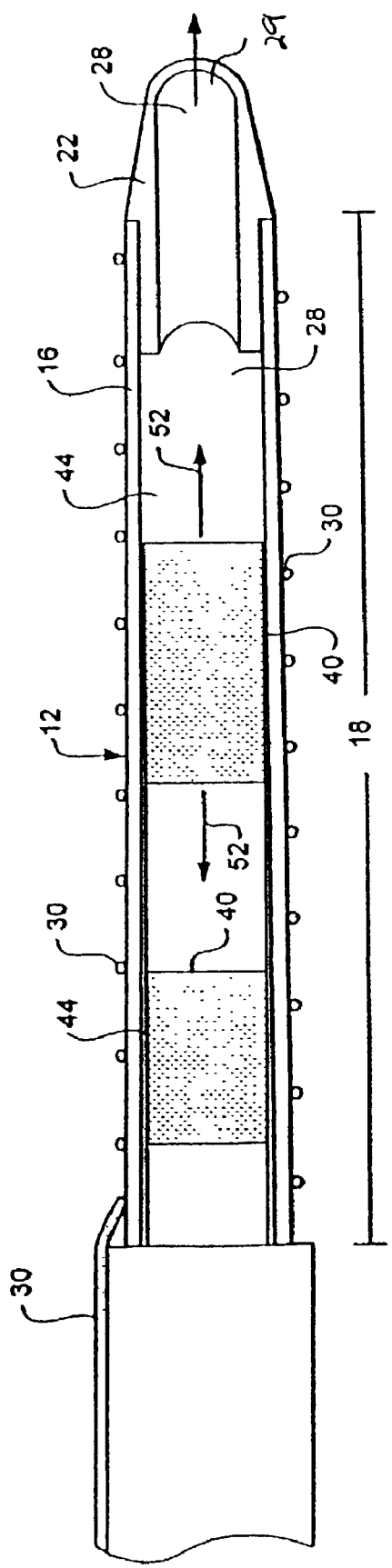
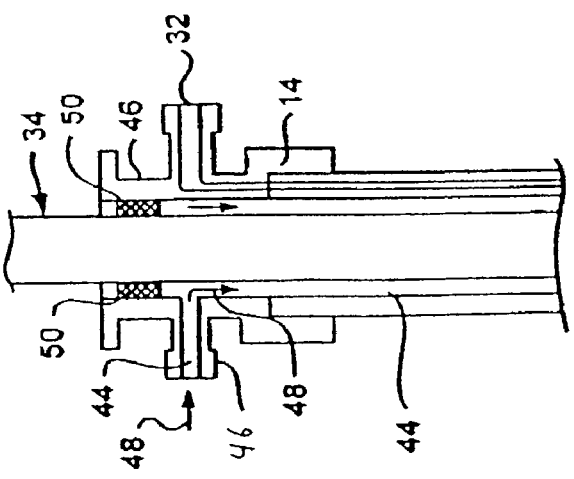
FIG. 2A
FIG. 2B

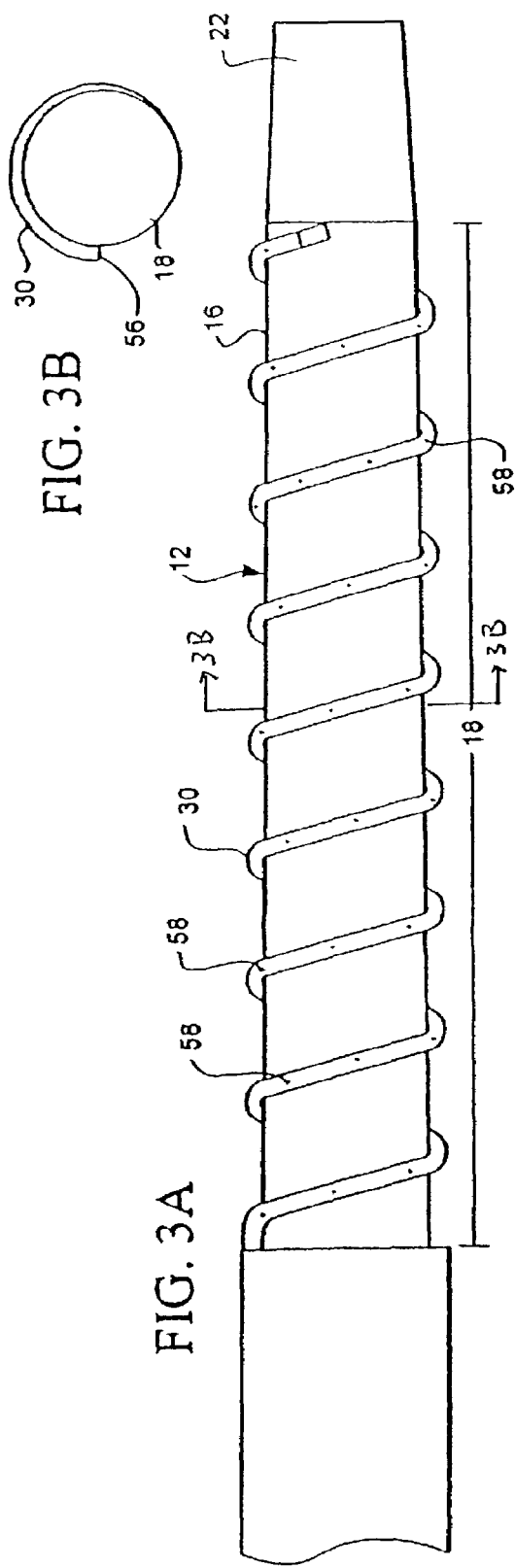
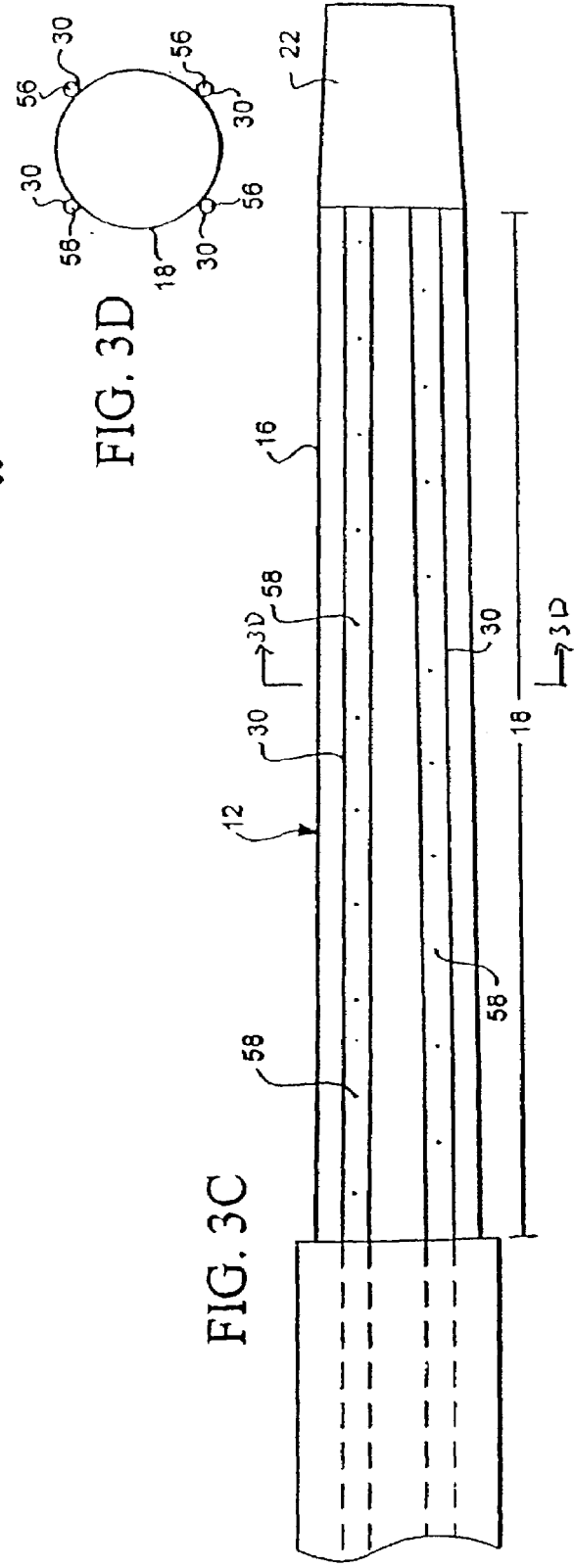

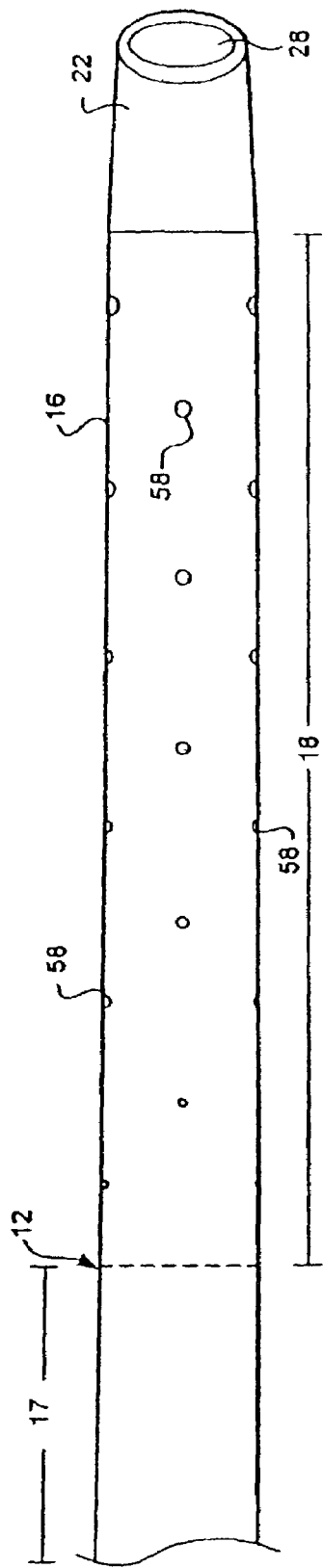
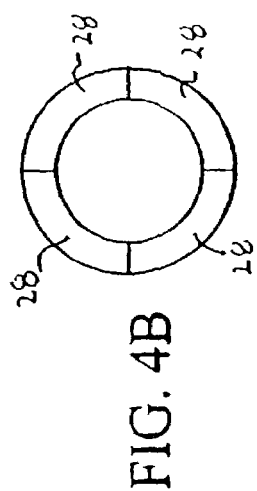
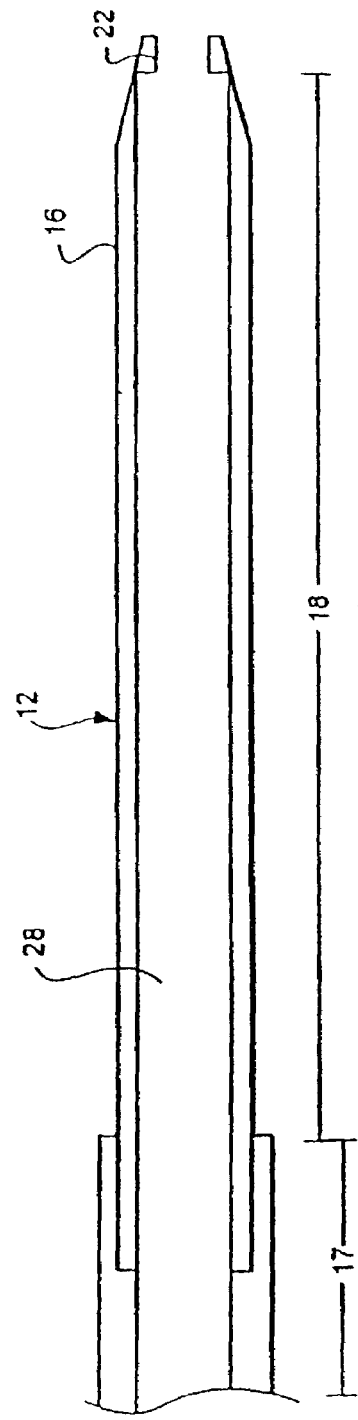
FIG. 4A
FIG. 4B
FIG. 5

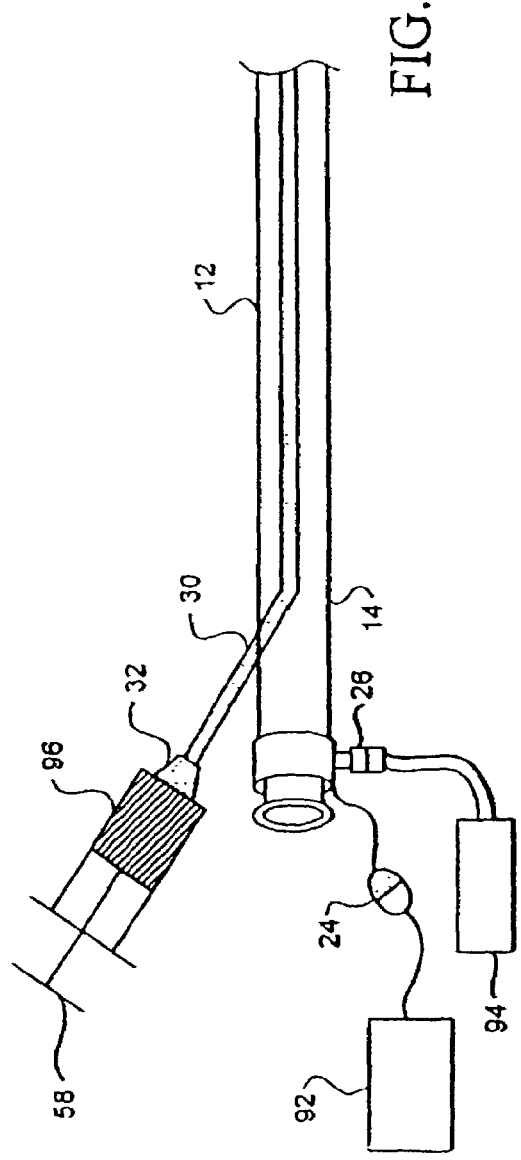
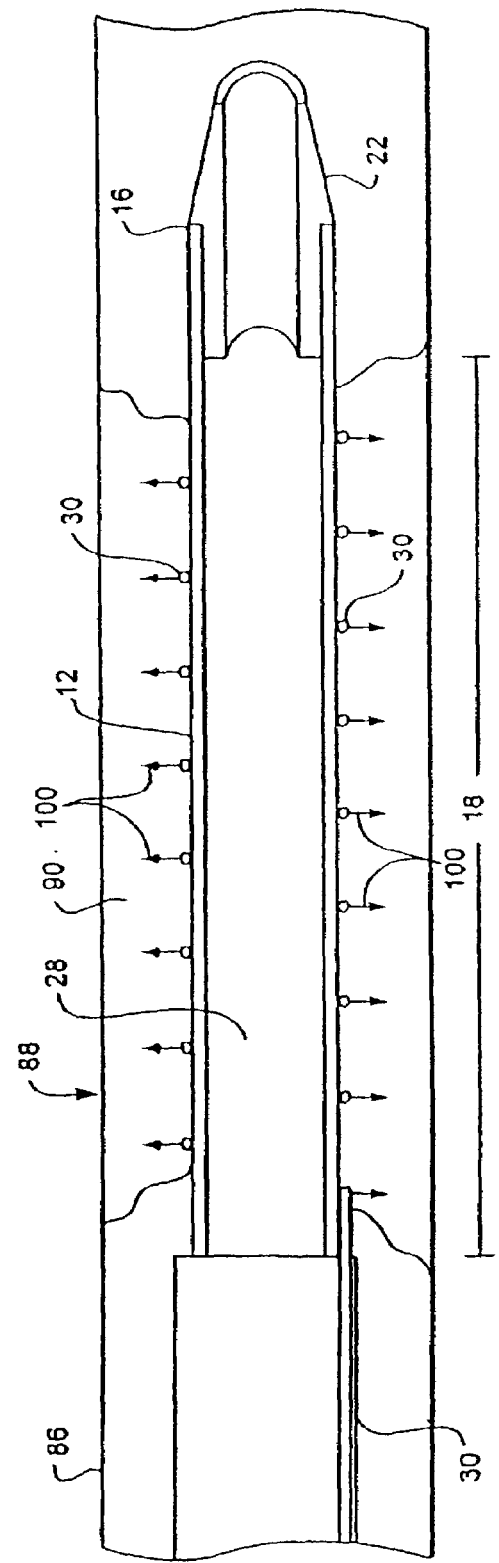
FIG. 10D
FIG. 10E

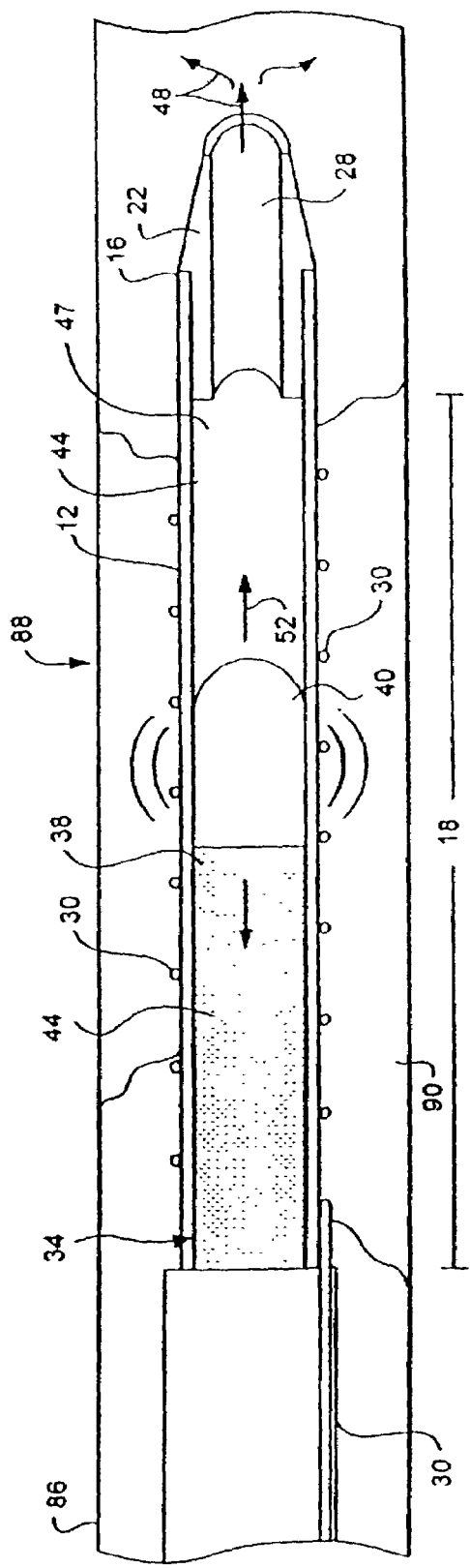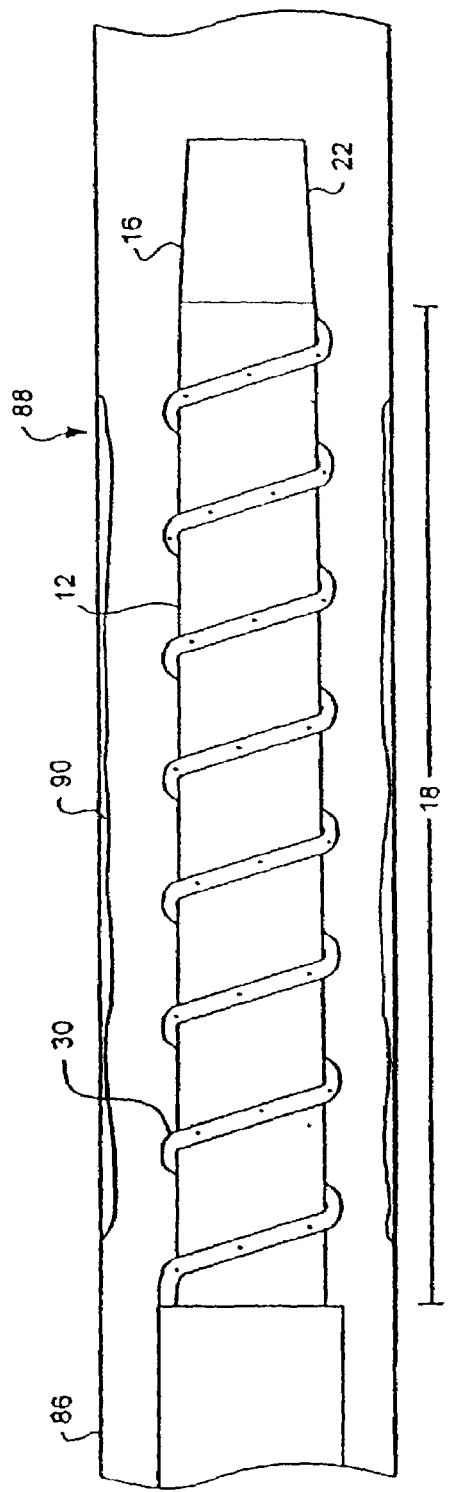
FIG. 10F
FIG. 10G

ALTERNATE SITE GENE THERAPY

RELATED APPLICATIONS

This application claims priority to U.S. provisional application No. 60/340,745, filed Dec. 11, 2001 which is incorporated by reference in its entirety.

BACKGROUND OF THE INVENTION

1. Field of the Invention

Preferred embodiments of the present invention relate to catheters having an ultrasonic assembly. The apparatus is particularly well suited for using ultrasonic energy to enhance the therapeutic effects and/or delivery of drugs including nucleotides (DNA, RNA, and analogs thereof), medication, and other therapeutic compounds at a treatment site within the body.

2. Description of the Related Art

Several therapeutic and diagnostic applications use ultrasonic energy. For example, ultrasonic energy can be used to enhance the delivery and therapeutic effect of various therapeutic compounds. See e.g., U.S. Pat. Nos. 4,821,740, 4,953,565 and 5,007,438. In some applications, it is desirable to use an ultrasonic catheter to deliver the ultrasonic energy and/or therapeutic compound to a specific site in the body. Such an ultrasonic catheter typically includes an ultrasonic assembly for generating the ultrasonic energy. The ultrasonic catheter can also include a delivery lumen for delivering the therapeutic compound to the treatment site. In this manner, the ultrasonic energy can be used at the treatment site to enhance the desired therapeutic effects and/or delivery of the therapeutic compound.

Ultrasonic catheters have successfully been used to treat human blood vessels that have become occluded or completely blocked by plaque, thrombi, emboli or other substances that reduce the blood carrying capacity of the vessel. See e.g., U.S. Pat. No. 6,001,069. To remove the blockage, the ultrasonic catheter is used to deliver solutions containing dissolution compounds directly to the blockage site. The ultrasonic energy generated by the catheter enhances the therapeutic effects of the dissolution compounds.

Ultrasonic catheters can also be used to perform gene therapy on an isolated region of a body lumen. Gene therapy may include introduction of a gene into one or more cells to provide a gene product either not normally produced by the a cell or produced in insufficient quantities. Gene therapy also includes inhibition of the expression of an endogenous gene by antisense or co-suppression. Gene therapy may also be accomplished using molecular decoys which provide binding sites for cellular factors and thus operate as suicide molecules. As disclosed in U.S. Pat. No. 6,135,976, which is incorporated herein by reference, an ultrasonic catheter can be provided with one or more expandable sections for occluding a section of the body lumen. A gene therapy composition is delivered to the occluded section through the delivery lumen of the catheter. The ultrasonic assembly delivers ultrasonic energy to the occluded section to enhance the entry of the gene composition into the cells of the occluded section. Other uses for ultrasonic catheters include delivering and activating light activated drugs (see e.g., U.S. Pat. No. 6,176,842).

The various embodiments of the methods, devices and kits disclosed in U.S. Pat. No. 6,135,976, entitled METHOD, DEVICE AND KIT FOR PERFORMING GENE THERAPY, teach approaches to performing gene therapy at the treatment site. More specifically, U.S. Pat. No. 6,135,976 discloses approaches to performing gene therapy directly on a selected region of the body lumen. A region of the body lumen may be selected for treatment for numerous reasons, such as when the region is injured or diseased and in need of therapy. U.S. Pat. No. 6,135,976 is incorporated by reference herein and made a part of this specification.

Sometimes, however it is undesirable or impossible to perform gene therapy directly at an injured or diseased region of the body lumen. What is needed is an approach to performing gene therapy at an alternate site when it is undesirable or impossible to perform gene therapy at the injured or diseased region of the body lumen.

SUMMARY OF THE INVENTION

In one embodiment, the present invention is directed to performing gene therapy on a tissue, organ or group of cells, in vivo, which are to be transplanted to a different part of the body. Thus in one embodiment, a method is described for performing gene therapy on a selected section of a body lumen including the steps of:

placing within a selected section of the body lumen a catheter including one or more expandable members for occluding sections of the body lumen proximal and/or distal to the selected section;

occluding sections of the body lumen proximal and/or distal to the selected section of the body lumen;

delivering a gene therapy composition into the selected section of the body lumen;

delivering ultrasound to the selected section of the body lumen for a period of time in the presence of the gene therapy composition under conditions where the ultrasound causes cavitation of cells in the selected section; and transplanting the selected section of the body lumen into another region of the body.

In one embodiment, the selected section of body lumen is highly vascularized. In a preferred embodiment, the selected section of body lumen is capable of anaerobic metabolism. Preferably, the selected section of the body lumen is highly vascularized and capable of anaerobic metabolism. In one embodiment, the selected section of the body lumen is a blood vessel of leg skeletal muscle.

In a preferred embodiment, the gene therapy composition comprises a gene operably linked to a promoter for expression in one or more cells within the selected section of the body lumen. The gene may produce a gene product which reduces the immune response to grafts or a gene product which blocks cell proliferation. In some embodiments, the gene therapy composition includes an oligonucleotide. The oligonucleotide may act to inhibit expression of an endogenous gene product by either antisense or co-suppression.

Further aspects, features and advantages of this invention will become apparent from the detailed description of the preferred embodiments which follow.

BRIEF DESCRIPTION OF THE DRAWINGS

FIG. 1A is side elevation view of one embodiment of an ultrasonic catheter particularly suited for long segment peripheral arterial occlusions such as those in the arteries of the leg.

FIG. 1B is a side elevation view of an inner core of the ultrasonic catheter of FIG. 1A.

FIG. 2A is a cross-sectional view of a distal end of the ultrasonic catheter of 1A.

FIG. 2B is a cross-sectional view of a proximal end of the ultrasonic catheter of FIG. 1A.

FIG. 3A is a side view of the distal end of the ultrasonic catheter of FIG. 1A.

FIG. 3B is a cross-sectional view of the distal end of the ultrasonic catheter of FIG. 3A.

FIG. 3C is a side view of a modified embodiment of the distal end of an ultrasonic catheter.

FIG. 3D is a cross-sectional view of the distal end of the ultrasonic catheter of FIG. 3C.

FIG. 4A is a side view of still yet another modified embodiment of the distal end of an ultrasonic catheter which includes drug delivery ports of increasing size.

FIG. 4B is a cross-sectional view of a distal end of an ultrasonic catheter wherein the proximal and distal ends are made of different materials.

FIG. 5 is a cross-sectional view of a distal end of an ultrasonic catheter that includes an integral occlusion device.

FIG. 10D is a side view of the proximal end of the ultrasonic catheter of FIG. 10B.

FIG. 10E is a cross-sectional view of the distal end of the ultrasonic catheter of FIG. 10B positioned at the treatment site.

FIG. 10F is a cross-sectional view of the distal end of the ultrasonic catheter of FIG. 10B positioned at the treatment site showing the movement of the inner core.

FIG. 10G is a side view of the distal end of the ultrasonic catheter of FIG. 10B positioned at the treatment site.

DETAILED DESCRIPTION OF PREFERRED EMBODIMENTS

Figure 1C:
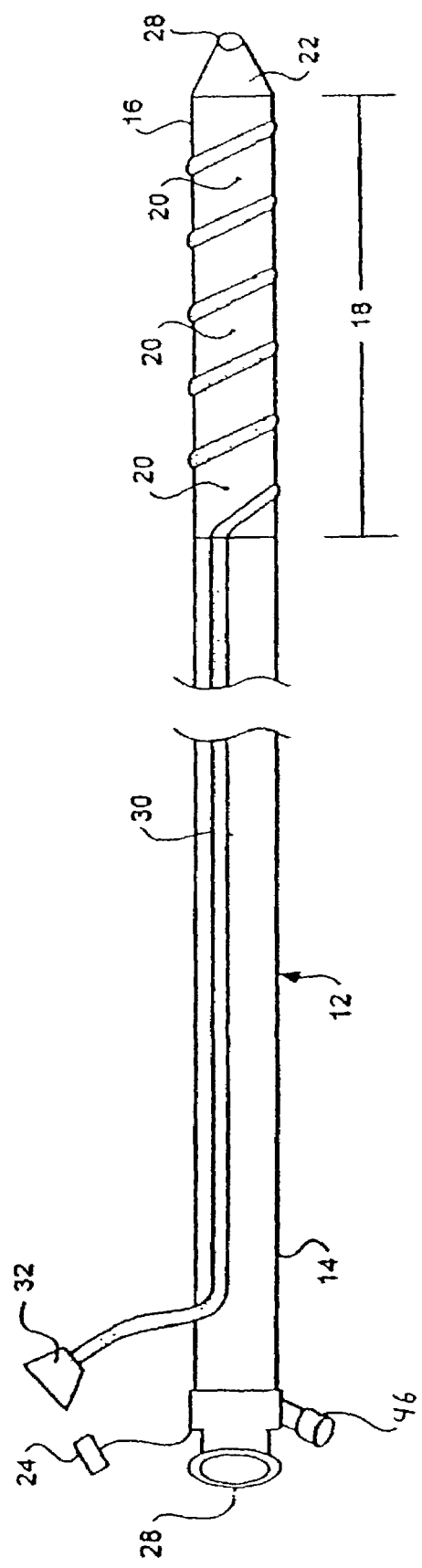
FIG. 1C is a side elevation view of a modified embodiment of an ultrasonic catheter.

Certain preferred embodiments of the present invention described herein provide for an ultrasonic catheter and methods of using such an ultrasonic catheter. The ultrasonic catheter can be used to enhance the therapeutic effects of drugs, medication and other pharmacological agents at a specific site within the body. See e.g., U.S. Pat. Nos. 5,318,014, 5,362,309, 5,474,531, 5,628,728, 6,001,069, and 6,210,356. In one preferred embodiment, the ultrasonic catheter is adapted for use in the treatment of thrombus in the small blood vessels of the human body, such as, for example, the small cerebral arteries. In another embodiment, the ultrasonic catheter is adapted for use in the treatment of thrombus in larger blood vessels or arteries such as those located in the lower leg. However, the ultrasonic catheters disclosed herein may also find utility in other therapeutic applications, such as, for example, performing gene therapy (see e.g., U.S. Pat. No. 6,135,976), activating light activated drugs used to cause targeted tissue death (see e.g., U.S. Pat. No. 6,176,842) and causing cavitation to produce biological effects (see e.g., U.S. Pat. No. RE36,939). Moreover, such therapeutic applications may be used in various human tissues, such as, for example, other parts of the circulatory system, solid tissues, duct systems and body cavities. It is also anticipated that the ultrasonic catheters disclosed herein may find utility in other medical applications, such as, for example, diagnostic and imaging applications.

Other uses for the ultrasonic catheters and methods disclosed herein may include applications where the ultrasonic energy provides a therapeutic effect by itself, such as, for example, preventing and/or reducing stenosis and/or restenosis, tissue ablation, abrasion or disruption, promoting temporary or permanent physiological changes in intracellular or intercellular structures, or rupturing micro-balloons or micro-bubbles for drug delivery. See e.g., U.S. Pat. Nos. 5,269,291 and 5,431,663. The methods and apparatus disclosed herein may also find utility in applications that do not require the use of a catheter, such as, for example, enhancing hyperthermic drug treatment or using an external ultrasonic source to enhance the therapeutic effects of drugs, medication and other pharmacological agents at a specific site within the body or to provide a therapeutic or diagnostic effect by itself. See e.g., U.S. Pat. No. 4,821,740, 4,953,565, 5,007,438 and 6,096,000.

The entire disclosure of all of the patents mentioned in the previous two paragraphs are hereby incorporated by reference herein and made a part of this specification.

As used herein, the term "ultrasonic energy" is a broad term and is used in its ordinary sense and means, without limitation mechanical energy transferred through longitudinal pressure or compression waves with a frequency greater than about 20 KHz and less than about 20 MHz. In one embodiment, the waves have a frequency between about 500 KHz and 20 MHz and in another embodiment between about 1 MHz and 3 MHz. In yet another embodiment, the waves have a frequency of about 3 MHz.

As used herein, the term "catheter" is a broad term and is used in its ordinary sense and means, without limitation a flexible tube configured to be inserted into a body cavity, duct or vessel.

As used herein, the term "drug" includes gene therapy agents. A gene therapy agent refers to a composition containing a nucleic acid. DNA, RNA, and analogs thereof are encompassed by the term nucleic acid. The nucleic acid containing composition may contain one or more than one nucleic acid species. Both oligonucleotides and polynucleotides are encompassed herein. The nucleic acid composition may include a construct or expression vector, including constructs and expression vectors which are capable of transforming a cell in or adjacent to the body lumen. Transformation refers to the process of changing the genotype of a recipient cell by the introduction of RNA or DNA by whatever methodology available to one of ordinary skill in the art. Transformation may result in stable or transient expression of the nucleic acid material in the cell. Stable transformation means that the genetic material is present in the germ line and is passed to progeny cells. Transient transformation refers to nucleic acid material which may be expressed transiently but is not expressed in progeny of the transformed cell.

Examples of types of nucleic acid constructs which may be used as the gene therapy agent include, but are not limited to strands or duplexes of DNA and/or RNA, DNA and/or RNA viral vectors and plasmids.

The gene therapy agent may encode a gene product, i.e., a protein encoded by the nucleic acid construct which, when expressed in the cell, has a desired therapeutic effect on the cell. Examples of therapeutic effects which may be achieved include, but are not limited to, inducing cell growth, and inducing cell death. Of particular interest are gene therapy agents useful in affecting the immure response to a transplanted organ or group of cells.

The gene therapy agent may also include regulatory components such as promoters, enhancers and/or terminators which may be included on the expression vector. Regulation may involve increasing or decreasing the expression of the native protein by the cell. Regulation may also include expression of antisense DNA or RNA or co-suppression. The nucleic acid composition may include "naked" DNA or RNA, i.e., nucleic acid material that is not part of an expression vector.

Particular examples of gene therapy agents which may be used in the present invention include, but are not limited to those agents described in U.S. Pat. Nos. 5,719,131; 5,714,353; 5,656,465; 5,583,362; 5,399,346; 5,334,761; 5,283,185; 5,264,618; 5,252,479; 4,394,448; each of which are incorporated herein by reference in their entirety.

Transfection of a cell with a gene therapy agent can be facilitated through the use of a carrier in combination with the gene therapy agent. Various different carriers have been developed for performing this function. Examples of different carriers which may be used include, but are not limited to, cationic lipids (derivatives of glycerolipids with a positively charged ammonium or sulfonium ion-containing headgroup; e.g., U.S. Pat. No. 5,711,964); cationic amphiphiles (e.g., U.S. Pat. Nos. 5,719,131; 5,650,096); cationic lipids (e.g., U.S. Pat. Nos. 5,527,928; 5,283,185; 5,264,618); and liposomes (e.g., U.S. Pat. Nos. 5,711,964; 5,705,385; 5,631,237), each of the U.S. Patents listed above being incorporated herein by reference.

A microbubble booster may be used to facilitate entry of the gene therapy agent into cells. A wide variety of microbubble boosters have been developed for use in other ultrasound applications, any of which may be used in the present invention. The gene therapy agent may be separate from, attached to the surface of, or included within the microbubbles. The microbubble booster preferably comprises a liquid containing microbubbles of a gas having a diameter of 0.1 to 100 μm. The booster also preferably contains about $4 \times 10^7$ of the microbubbles per one milliliter of a liquid.

The microbubble booster may be formed by entrapping microspheres of a gas into a liquid. Microbubbles may be made using a variety of gases including, but not limited to air, oxygen, carbon dioxide, nitrogen, noble gases (e.g. xenon, krypton, argon, neon, helium, etc.), preferably air and oxygen gas. The liquid may include any liquid which can form microbubbles, for example, human serum albumin (e.g. 3 to 5% human serum albumin), a physiological saline solution, a 5% aqueous glucose solution, an aqueous indocyanine green solution, autoblood, an aqueous solution of maglumine diatriazoate (=renografin), and any other X-ray contrast medium).

The microbubble booster can be prepared by any known method. For example, the microbubble booster can be formed by agitating a suitable liquid while blowing a suitable gas into the liquid, or alternatively exposing the liquid to ultrasound with a sonicator under a gaseous atmosphere, whereby a vibration is given to the liquid to form microbubbles of the gas.

When the ultrasound is applied to in the presence of microbubbles, the microbubbles can act as a nucleus of cavitation and thereby the cavitation occurs more easily. This enables less ultrasonic energy to be used in order to achieve the desired amount of diffusion of the gene therapy agent into the cells.

The entire disclosure of all of the above-mentioned patents is hereby incorporated by reference herein and made a part of this specification.

I. Overview of a Long Segment Ultrasonic Catheter

FIGS. 1A and 1B illustrate one embodiment of an ultrasonic catheter 10, which is particularly suited for long segment peripheral arterial occlusions such as those in the arteries of the leg.

As shown in FIG. 1A, the ultrasonic catheter 10 generally comprises a multi component tubular body 12 having a proximal end 14 and a distal end 15. The tubular body 12 and other components of the catheter 10 can be manufactured in accordance with any of a variety of techniques well know in the catheter manufacturing field. Suitable material dimensions can be readily selected taking into account the natural and anatomical dimensions of the treatment site and of the desired percutaneous access site.

The elongate flexible body 12 comprises an outer sheath 16. The outer sheath 16 preferably includes a support section 17 located at the proximal end and an energy deliver section 18 located at the distal end of the catheter 10. In one embodiment, the support section 17 comprises extruded PTFE, PEEK, PE and/or similar materials that provide the outer sheath 16 with enough flexibility, kink resistance, rigidity and structural support necessary to push the energy delivery section 18 to a treatment site. In an embodiment particularly suited for treating thrombus in the arteries of the leg, the outer sheath 16 has an outside diameter of approximately 0.060 to 0.075 inches. In such, an embodiment, the outer sheath 16 has an axial length of approximately 90 centimeters.

The energy delivery section 18 of the outer sheath 16 is preferably made of a thinner material as compared to the support section 17. A thinner material is generally desirable because it increases the acoustic transparency of the energy delivery section 18. Suitable materials for the energy delivery section 18 include but are not limited to high or low density polyethylenes, urethanes, nylons, etc.

With reference to FIGS. 1A and 2A, the outer sheath 16 defines a utility lumen 28, which preferably extends through the length of the catheter 10. As shown in FIG. 1A, on the illustrated embodiment, the utility lumen 28 has a distal exit port 29 and a proximal access port 31. The proximal access port 31 is defined by a backend hub 33, which is attached to the proximal end 14 of the outer sheath 16.

With continued reference to FIG. 1A, a drug delivery member 30 is positioned adjacent the energy delivery section 18. The drug delivery member 30 includes a drug inlet port 32, which can be formed in the back end hub 33 and can be coupled with a drug source via a hub such as a Luer type fitting. The drug delivery member 30 can be incorporated into the support section 17 as illustrated in FIG. 1A or can be external to the support section as illustrated in FIG. 1C.

The catheter 10 also includes an elongated inner core 34 (see FIG. 1B) with a proximal end 36 and a distal end 38. An ultrasound radiating member 40 is positioned at the body distal end 38. The inner core 34 has an outer diameter which permits the inner core 34 to be inserted into the utility lumen 28 via the proximal access port 31. FIG. 2A illustrates the inner core 34 inserted inside the utility lumen 28 with the ultrasound radiating member 40 is positioned within the energy delivery section 18. Suitable outer diameters of the inner core 34 include, but are not limited to approximately 0.010–0.100 inches. Suitable diameters of the utility lumen 28 include, but are not limited to 0.015–0.110 inches.

The ultrasound radiating member 40 can be rotated or moved within the energy delivery section 18 as illustrated by the arrows 52 in FIG. 2A. The movement of the ultrasound radiating member 40 within the energy delivery section can be caused by manipulating the proximal end 36 of the inner core 34 while holding the back end hub 33 stationary. The inner core 34 is constructed, at least partially, from a material that provides enough structural support to permit movement of the inner core 34 within the sheath 16 without kinking of the outer sheath 16. Suitable materials for the inner core 34 include, but are not limited to polyimides, polyesters, polyurethanes, thermoplastic, elastomers, and braided wires or fiber reinforcement.

As illustrated in FIG. 2A, the outer diameter of the inner core 34 can be smaller than the diameter of the utility lumen 28 to create a cooling fluid lumen 44 between the inner core 34 and the utility lumen 28. A cooling fluid can flow through the cooling fluid lumen 44, past the ultrasound radiating member 40 and through the distal exit port 29. Cooling fluid can be supplied via a cooling fluid fitting 46 provided in the back end hub 33 shown in FIG. 1A. As will be explained below, the flow rate of the cooling fluid and/or the power to the ultrasound radiating member 40 can be adjusted to maintain the temperature of the ultrasound radiating member 40 within a desired range.

With reference to FIG. 2B, the cooling fluid can be flowed from the cooling fluid fitting 46 through the cooling fluid lumen 44 as illustrated by the arrows 48. The cooling fluid fitting 46 can include a hemostasis valve 50 with an inner diameter which substantially matches the diameter of the inner core 34. The matched diameters reduce leaking of the cooling fluid between the fitting 46 and the inner core 34.

Figure 2C:
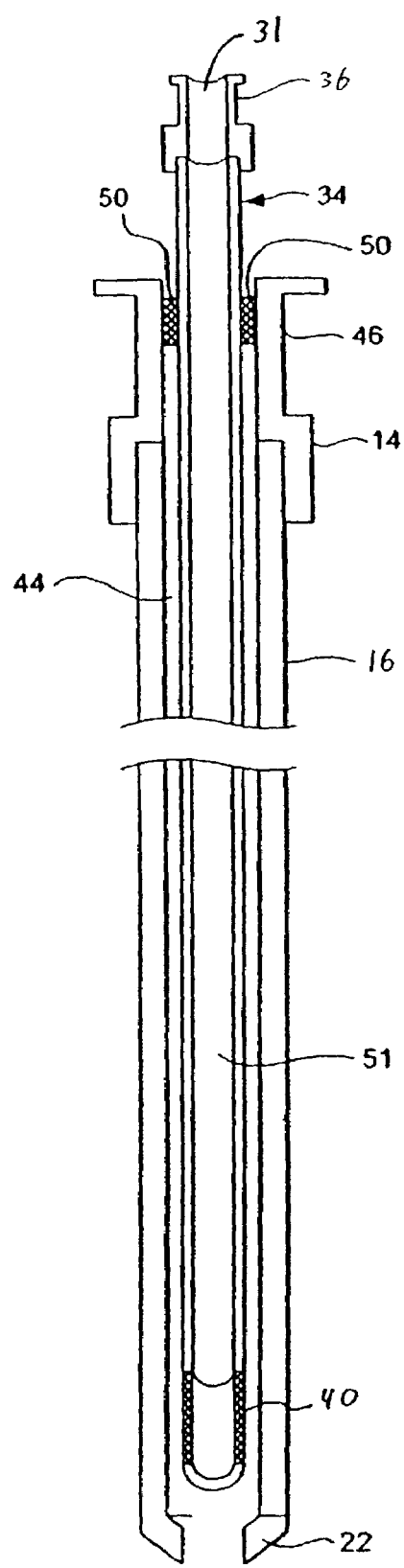
FIG. 2C is a cross-sectional view of another modified embodiment of an ultrasonic catheter.

As illustrated in FIG. 2C, in one embodiment, the ultrasound radiating member 40 can be a hollow cylinder and the inner core 34 can define a central lumen 51, which extends through the ultrasound radiating member 40. In such an embodiment, the cooling fluid can flow through the central lumen 51, pass and through the ultrasound radiating member 40 to provide cooling to the ultrasound radiating member 40. In such an arrangement, the cooling fluid can be supplied via the proximal port 31 with the a fitting 46 and a hemostasis valve 50 providing a seal between the inner core 34 and the outer sheath 16.

With reference back to FIG. 1A, the illustrated catheter includes an occlusion device 22, positioned at the distal end of the catheter 10. The utility lumen 28 preferably extends through the occlusion device 22. The portion of the utility lumen 28 extending through the occlusion device 22 has a diameter which can accommodate a guidewire (not shown) but which preferably prevents the ultrasound radiating member 40 from passing through the occlusion device 22. Suitable inner diameters for the occlusion device 22 include, but are not limited to 0.005–0.050 inches.

Figure 2D:
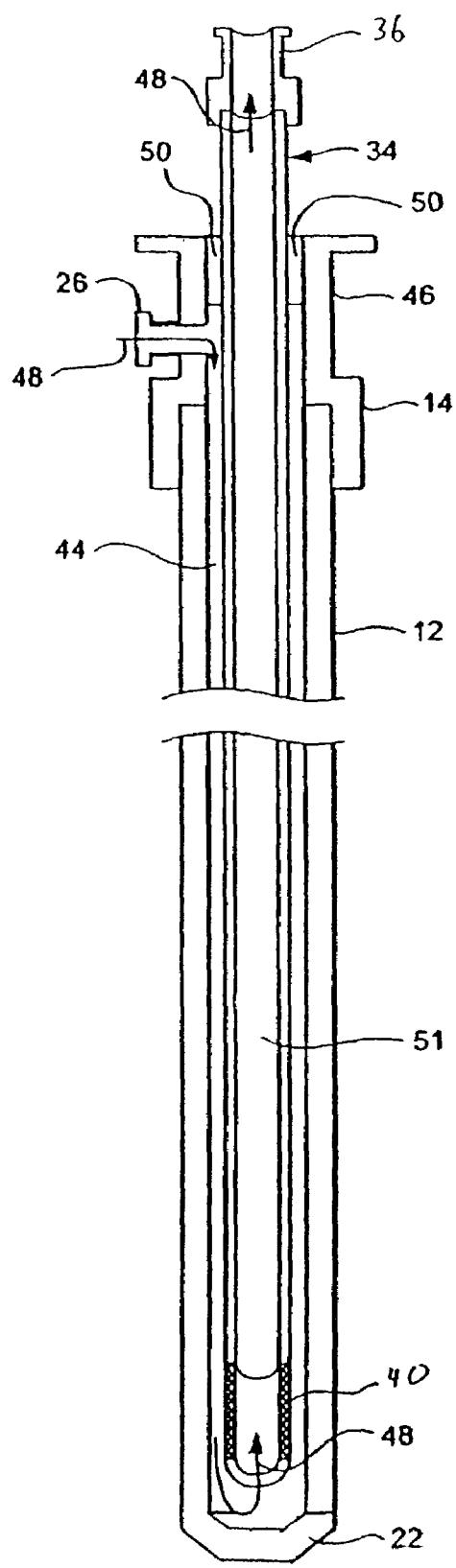
FIG. 2D is a cross-sectional view of yet another modified embodiment of an ultrasonic catheter.
Figure 2E:
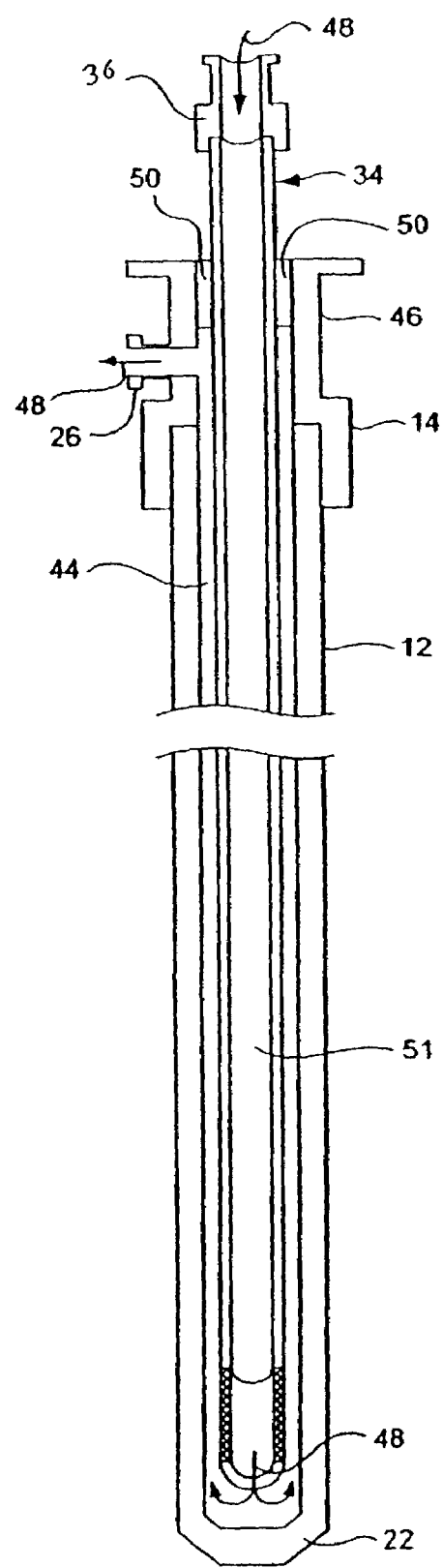
FIG. 2E is a cross-sectional view of still yet another modified embodiment of an ultrasonic catheter.

As illustrated in FIG. 2D, the occlusion device 22 can be integrally formed with the sheath 16 and can have a closed end. The central lumen 51 can serve as a return lumen for the cooling fluid. As a result, the inside and the outside of the ultrasound radiating member 40 are exposed to the cooling fluid to accelerate the cooling of the ultrasound radiating member 40. As illustrated in FIG. 2E, the flow of the cooling fluid can be reversed so the cooling lumen serves as the return cooling fluid lumen. The above cooling schemes permit the power provided to the ultrasound radiating member 40 to be increased in proportion to the cooling flow rate. Further, certain schemes can prevent exposure of the body to cooling fluids.

As illustrated in FIG. 3A, the drug delivery member 30 includes a drug delivery portion which is positioned adjacent the energy delivery section 18. As illustrated in FIG. 3B, the drug delivery member 30 includes a drug delivery lumen 56 extending through the length of the drug delivery member 30. The drug delivery member 30 also includes a series of drug delivery ports 58 coupled with the drug delivery lumen 56. A drug source coupled with the drug inlet port 32 can provide a pressure which drives a drug solution through the drug delivery lumen 56 and out the drug delivery ports 58. A suitable material for the drug delivery member 30 includes, but is not limited to high or low density polyethylenes, urethanes, nylons, etc.

The catheter 10 can include a plurality of drug delivery members 30. The drug delivery members 30 can be wound around the energy delivery section 18 or they can be positioned along the length of the energy delivery section 18 as illustrated in FIG. 3C. Each drug delivery member 30 can be coupled with the same drug inlet port 32. In another embodiment, each drug delivery member 30 is coupled with independent drug inlet ports 32 so different drug solutions can be delivered to different drug delivery ports 58.

The drug delivery ports 58 are preferably positioned close enough to achieve a substantially even flow of drug solution around the circumference of the energy delivery section 18 and along the length of the energy delivery sections 18. The proximity of adjacent drug delivery ports 58 can be changed by changing the density of drug delivery ports 58 along the drug delivery member 30, by changing the number of windings of the drug delivery member around the energy delivery section 18 or by changing the number of drug delivery members 30 included adjacent the energy delivery section 18. In one embodiment, the windings of the drug deliver members 30 has a pitch that ranges from about one spiral per one centimeter to about one spiral per 20 centimeters.

The size of the drug delivery ports 58 can be the same or vary along the length of the drug delivery member 30. For instance, the size of the drug delivery ports 58 distally positioned on the drug delivery section 18 can be larger than the size of the drug delivery ports 58 which are proximally positioned on the drug delivery section. The increase in size of the drug delivery ports 58 can be designed to produce similar flow rates of drug solution through each drug delivery port 58. This similar flow rate increases the uniformity of drug solution flow rate along the length of the sheath 16. In one embodiment in which the drug delivery ports 58 has similar sizes along the length of the drug delivery member, the drug delivery port 58 have a diameter of approximately 0.0005 to 0.0050 inches. In another embodiment in which the size of the drug delivery ports 58 changes along the length of the drug delivery member 30, the drug delivery ports have a diameter of approximately 0.0001" to 0.005 inches at the proximal end and about 0.0005 to 0.020 inches at the distal end. The increase in size between adjacent drug delivery ports can be substantially uniform between or along the drug delivery member 30. The dimensional increase of the drug delivery ports is dependent upon material and diameter of the drug delivery member. The drug delivery ports 58 can be punched, drilled, burnt with a laser, etc. into the drug delivery member 30.

Figure 3E:
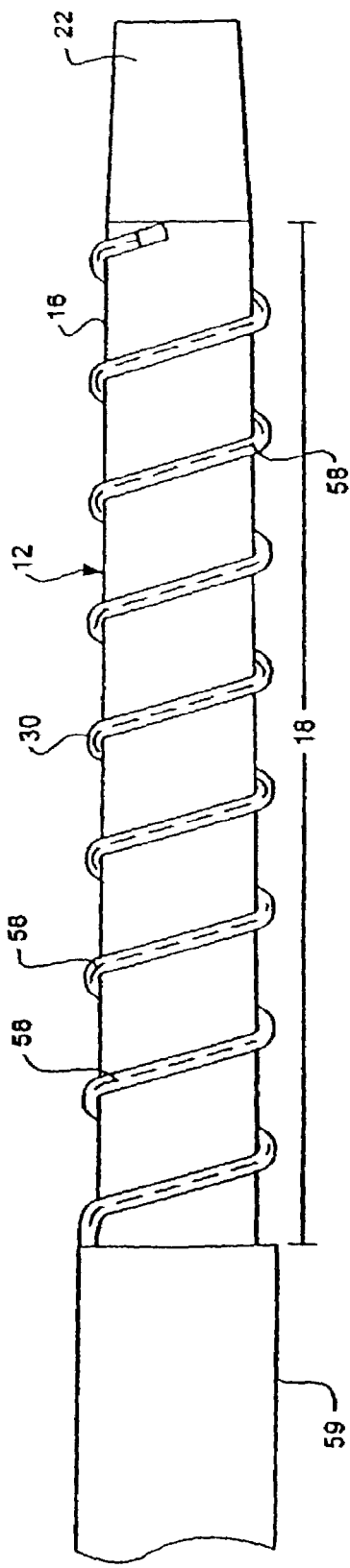
FIG. 3E is a side view of another modified embodiment of the distal end of an ultrasonic catheter.
Figure 3F:
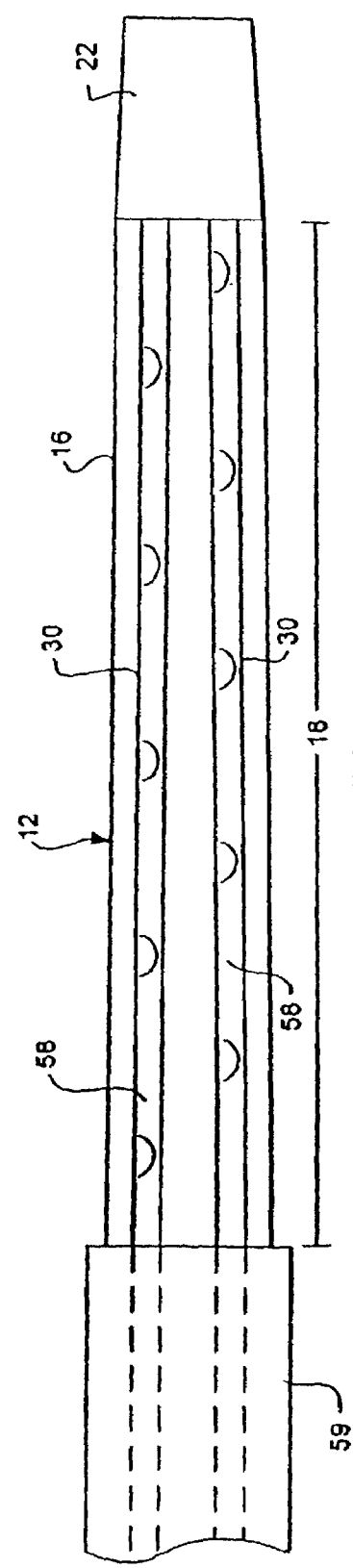
FIG. 3F is a side view yet of another modified embodiment of the distal end of an ultrasonic catheter.

Uniformity of the drug solution flow along the length of the sheath 16 can also be increased by increasing the density of the drug delivery ports 58 toward the distal end of the drug delivery member. The drug delivery ports 58 can be slits with a straight shape as illustrated in FIG. 3E or an arcuate shape as illustrated in FIG. 3F. The drug delivery member 30 can be constructed from materials such as polyimide, nylon, pebax, polyurethane or silicon. When the drug delivery lumen 56 is filled with drug solution, the slits remain closed until the pressure within the drug delivery lumen exceeds a threshold pressure. As the pressure within the drug delivery lumen builds, the pressure on each of the slits will be approximately uniform. Once the threshold pressure is reached, the uniform pressure will result in the slits opening almost simultaneously and cause a nearly uniform flow of drug solution out of all the slits. When the pressure within the drug delivery lumen 56 falls below the threshold pressure, the slits close and prevent delivery of additional drug solution. The stiffer the material used to construct the drug delivery member, the higher the threshold pressure required to open the slit shaped drug delivery ports. The slit shape can also prevent the drug delivery ports 58 from opening when exposed to low pressures from outside the sheath 16. As a result, slit shaped drug delivery ports can maximize control of drug delivery.

In the embodiment illustrated in FIG. 4A, the sheath 16 and energy delivery section 18 are constructed from a single material. Suitable materials include, but are not limited to high or low density polyethylenes, urethanes, nylons, etc. The entire sheath 16 or only the sheath proximal end may be reinforced by braiding, mesh or other constructions to increase pushability. As illustrated in FIG. 4A, the drug delivery ports 58 can be included in the sheath 16. The drug delivery ports 58 can be coupled with independent drug delivery lumens 28 formed by the outer sheath 16 as illustrated in FIG. 4B.

In the embodiment illustrated in FIG. 5, the sheath includes a support section 17 which is constructed from a different material than the energy delivery section 18. As mentioned above, the energy delivery section 18 can be constructed from a material which readily transmits ultrasound energy. The support section 17 can be constructed from a material which provides structural strength and kink resistance. Further, the support section or the proximal end of the support section may be reinforced by braiding, mesh or other constructions to increase kink resistance, and pushability. Suitable materials for the support section include, but are not limited to PTFE, PEEK, PE and/or similar materials. A suitable outer diameter for the support section includes, but is not limited to 0.020" to 0.200". Suitable materials for the energy delivery section 18 include, but are not limited to high or low density polyethylenes, urethanes, nylons, etc and other materials that produce minimal ultrasound attenuation. Such materials readily transmit ultrasound energy with minimal absorption of the ultrasound energy. FIG. 5 also illustrates the occlusion device 22 as being integrally formed with the energy delivery section 18.

Figure 6A:
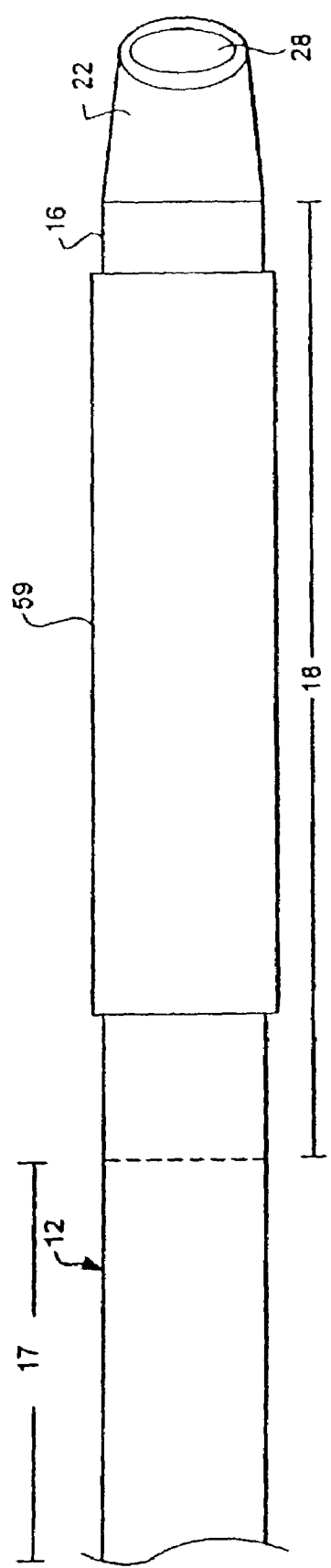
FIG. 6A is a side view of a distal end of an ultrasonic catheter, which includes a balloon device.

In the embodiment illustrated in FIG. 6A, the distal end 16 of the catheter includes a balloon device 59. The balloon device 59 can be constructed from permeable membrane or a selectively permeable membrane which allows certain media to flow through the membrane while preventing other media from flowing through the membrane. Suitable materials for the balloon device 59 include, but are not limited to cellulose, cellulose acetate, polyvinylchloride, polyolefin, polyurethane and polysulfone. When the balloon device 59 is constructed from a permeable membrane or a selectively permeable membrane, the membrane pore sizes are preferably 5 A-2 µm, more preferably 50 A-900 A and most preferably 100 A-300 A in diameter.

Figure 6B:
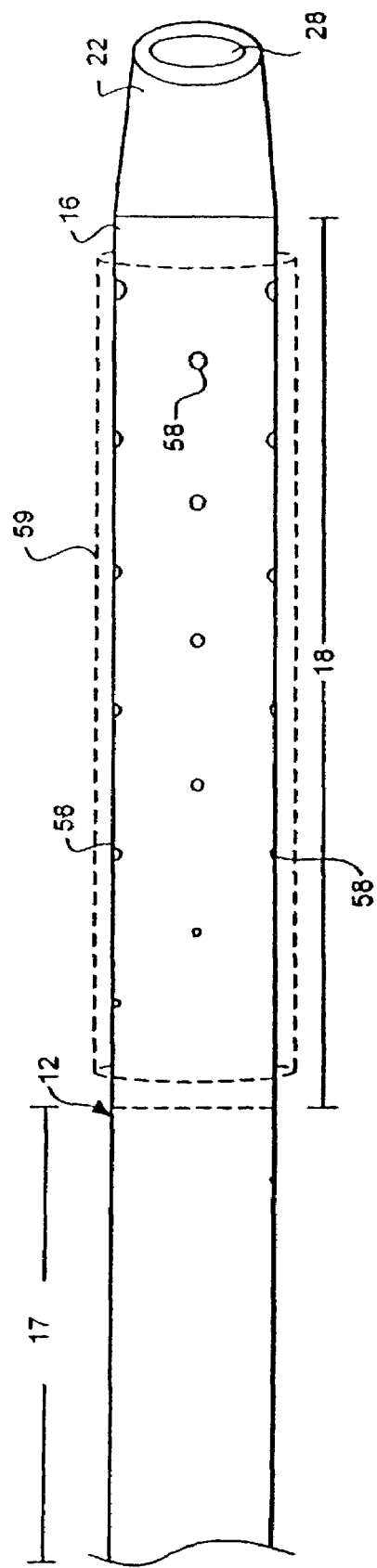
FIG. 6B is a cross-sectional view of a distal end of an ultrasonic catheter, which includes a balloon device and drug delivery ports configured to produce an even flow along the length of an energy delivery section.

As illustrated in FIG. 6B, the balloon device 59 can be positioned adjacent drug delivery ports 58. The drug delivery ports 58 can be designed so a uniform flow occurs along the length of the energy delivery section 18. This design can serve to prevent a pressure gradient from developing along the length of the balloon device. Delivering a drug solution through the drug delivery ports 58, can serve to expand the balloon device 59. When the balloon device 59 is constructed from a membrane or a selectively permeable membrane, the drug solution can be delivered with enough pressure to drive the drug across the membrane. Various phoretic processes and apparatuses can also be used to drive the drug solution across the membrane. When the balloon device 59 is constructed from a selectively permeable membrane, the pressure and/or phoresis may drive only certain components of the drug solution across the membrane while preventing other components from crossing the membrane.

Figure 6C:
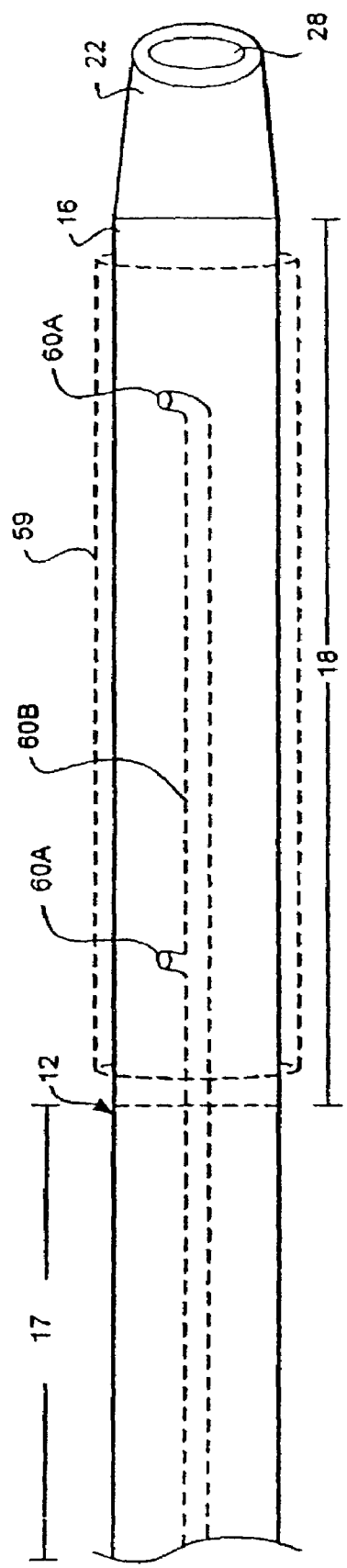
FIG. 6C is a cross-sectional view of a distal end of an ultrasonic catheter, which includes a balloon device and an expansion lumen for expanding the balloon device and delivering a drug solution.

The balloon device 59 can also be positioned adjacent one or more expansion ports 60A coupled with an expansion lumen 60B as illustrated in FIG. 6C. The drug solution can be delivered to the balloon 59 via the expansion lumen 60B. Delivering a drug solution through the expansion lumen 60B can serve to expand the balloon device 59. When the balloon device 59 is constructed from a membrane or a selectively permeable membrane, the drug can be delivered with enough pressure to drive the drug solution or certain components of the drug solution across the membrane. Similarly, phoretic means can also be used to drive the drug solution or certain components of the drug solution across the membrane.

Figure 6D:
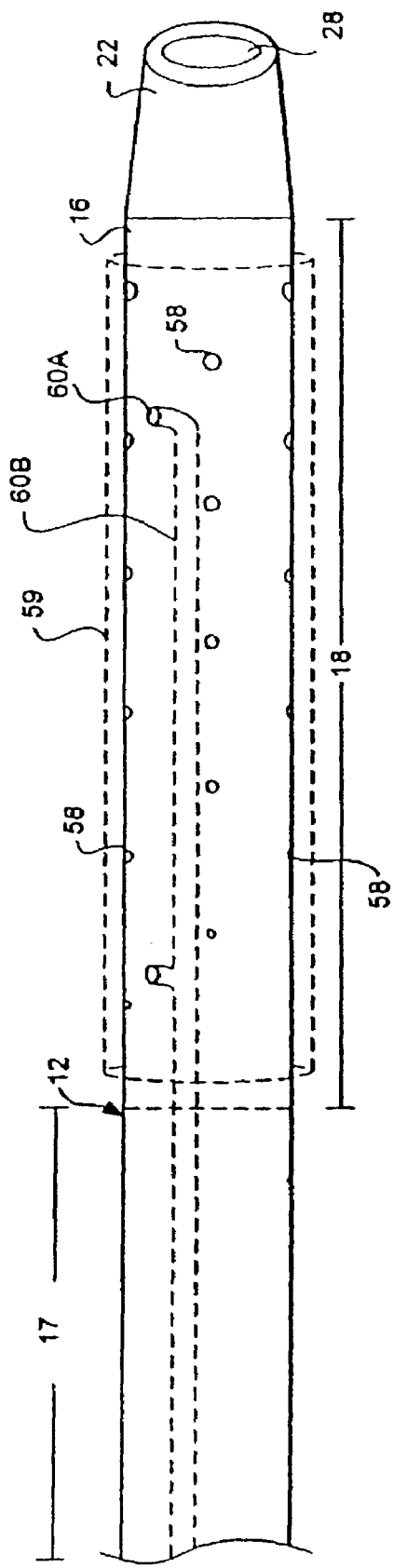
FIG. 6D is a cross-sectional view of a distal end of an ultrasonic catheter, which includes a balloon device and an expansion lumen for expanding the balloon device and drug delivery delivering ports configured to produce an even flow along an energy delivery section.

The balloon device 59 can also be positioned adjacent expansion ports 60A coupled with an expansion lumen 60B and drug delivery ports 58 as illustrated in FIG. 6D. Different drug solutions can be delivered through the expansion ports 60B and the drug delivery ports 58. Further, a media suitable for expanding the balloon device 59 can be delivered through the expansion lumen 60B and the expansion ports 60A while the drug solution can be delivered through the drug delivery ports 58. When the balloon device 59 is constructed from a membrane or a selectively permeable membrane, a medium which wets the membrane and enhances the permeability of the membrane can be delivered through the expansion ports 60A. A drug solution can be delivered through the drug delivery ports 58 concurrently with or after the wetting medium has been delivered.

In the illustrated embodiment, the ultrasound radiating member 40 comprises an ultrasonic transducer, which converts, for example, electrical energy into ultrasonic energy. A suitable example of an ultrasonic transducer for generating ultrasonic energy from electrical energy includes, but is not limited to, piezoelectric ceramic oscillators. In a modified embodiment, the ultrasound energy can be generated by an ultrasonic transducer that is remote from the ultrasound radiating member 40 and the ultrasonic energy can be transmitted via, for example, a wire to the ultrasound radiating member 40.

In the illustrated embodiment, the ultrasound radiating member 40 comprises an ultrasonic transducer that has a cylindrical shape. In other embodiments, the transducer can be a block, a hollow cylinder or a disk that are or are not concentric with the inner core 34. The ultrasound radiating member 40 can also be formed from an array of smaller ultrasound radiating members. Similarly, a single ultrasound radiating member 40 can be formed from a combination of several smaller ultrasound radiating members.

As mentioned above, suitable frequencies for the ultrasound radiating member 40 include, but are not limited to, from about 20 KHz and less than about 20 MHz. In one embodiment, the frequency is between about 500 KHz and 20 MHz and in another embodiment between about 1 MHz and 3 MHz. In yet another embodiment, the sound waves have a frequency of about 3 MHz.

Figure 7A:
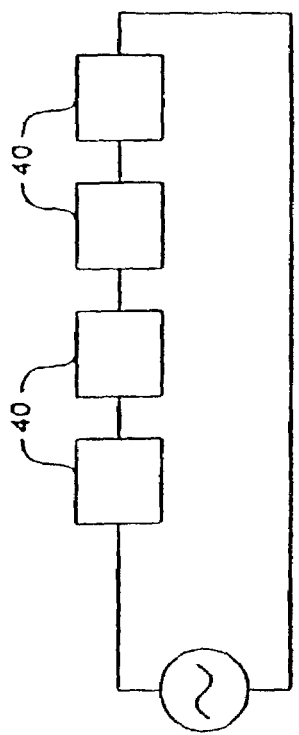
FIG. 7A illustrates a wiring diagram for connecting a plurality of ultrasound radiating members in parallel.
Figure 7B:
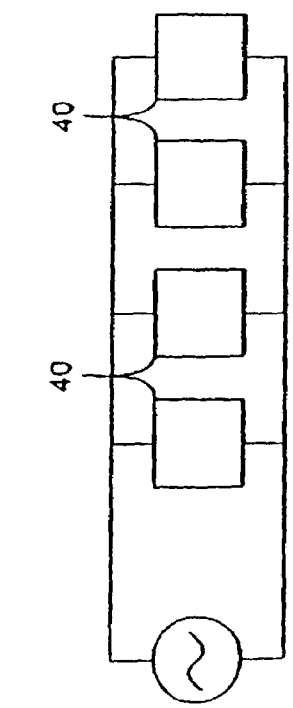
FIG. 7B illustrates a wiring diagram for connecting a plurality of ultrasound radiating members in series.

In one embodiment, each ultrasound radiating member 40 can be individually powered. When the inner core 34 includes N ultrasound radiating members 40, the inner core 34 includes 2N wires to individually power N ultrasound radiating members 40. The individual ultrasound radiating members 40 can also be electrically coupled in serial or in parallel as illustrated in FIGS. 7A and 7B. These arrangements permit more flexibility as they require only fewer wires. Each of the ultrasound radiating members 40 can receive power simultaneously whether the ultrasound radiating members 40 are in series or in parallel. When the ultrasound radiating members 40 are in series, less current is required to produce the same power from each ultrasound radiating member 40 than when the ultrasound radiating members 40 are connected in parallel. The reduced current allows smaller wires to be used to provide power to the ultrasound radiating members 40 and accordingly increases the flexibility of the inner core 34. When the ultrasound radiating members 40 are connected in parallel, an ultrasound radiating member 40 can fracture without breaking the current flow and the remaining ultrasound radiating members 40 will continue to operate.

Figure 7C:
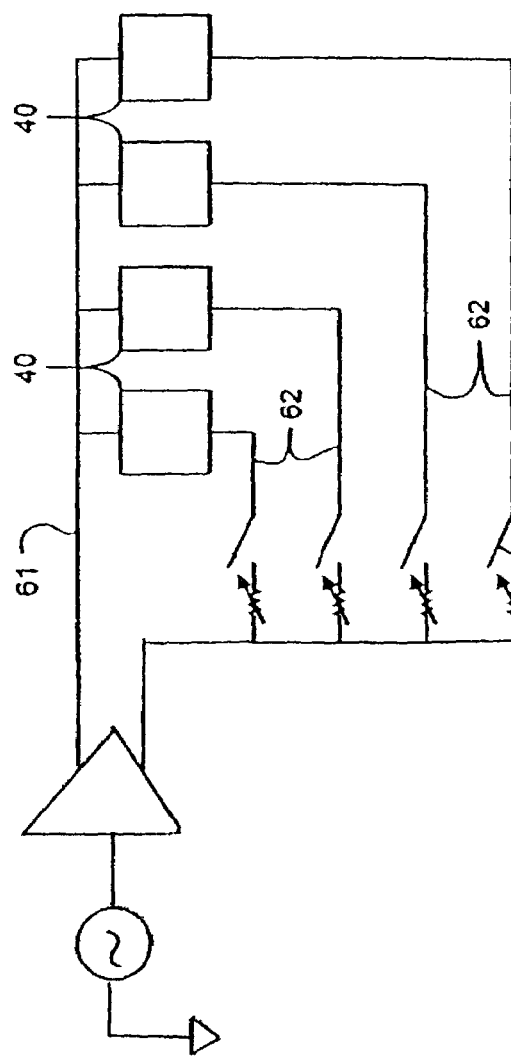
FIG. 7C illustrates a wiring diagram for connecting a plurality of ultrasound radiating members with a common wire.

Preferably, the output power of the ultrasound radiating members 40 can be controlled. For example, as illustrated in FIG. 7C, a common wire 61 can provide power to each ultrasound radiating member 40 while each ultrasound radiating member 40 has its own return wire 62. A particular ultrasound radiating member 40 can be individually activated by closing a switch 64 to complete a circuit between the common wire 61 and the particular ultrasound radiating member's return wire 62. Once a switch 64 corresponding to a particular ultrasound radiating member 40 has been closed, the amount of power supplied to the ultrasound radiating member 40 can be adjusted. Accordingly, an inner core 34 with N ultrasound radiating members 40 requires only N+1 wires and still permits independent control of the ultrasound radiating members 40. This reduced number of wires increases the flexibility of the inner core 34. To improve the flexibility of the inner core 34, the individual return wires 62 can have diameters which are smaller than the common wire 61 diameter. For instance, in an embodiment where N ultrasound radiating members 40 will be powered simultaneously, the diameter of the individual return wires 62 can be approximately the square root of N times smaller than the diameter of the common wire 61.

As illustrated in FIG. 1B, the inner core 34 of the catheter 10 can include one or more temperature sensors 20, preferably located at the distal end 38. The proximal end 36 can include a temperature sensor lead 24, which is operatively connected to the temperature sensors. In a modified embodiment illustrated in FIG. 1C, the temperature sensors 20 can be positioned in the energy delivery section 18 on the surface of the outer sheath 16. In such an arrangement, the temperature sensor lead 24 extends from the proximal 14 end of the outer sheath 16. Suitable temperature sensors 20 include, but are not limited to temperature sensing diodes, thermistors, thermocouples, resistance temperature detectors (RTDs), and fiber optic temperature sensors which use thermalchromic liquid crystals. Suitable temperature sensor 20 geometries include, but are not limited to, a point, patch, stripe and a band around the sheath 16. The temperature sensors 20 can be positioned on the sheath 16 or on the inner core 34 near the ultrasound radiating members 40. The temperature sensors 20 are preferably positioned so they are exposed near the energy deliver section 18.

Figure 8:
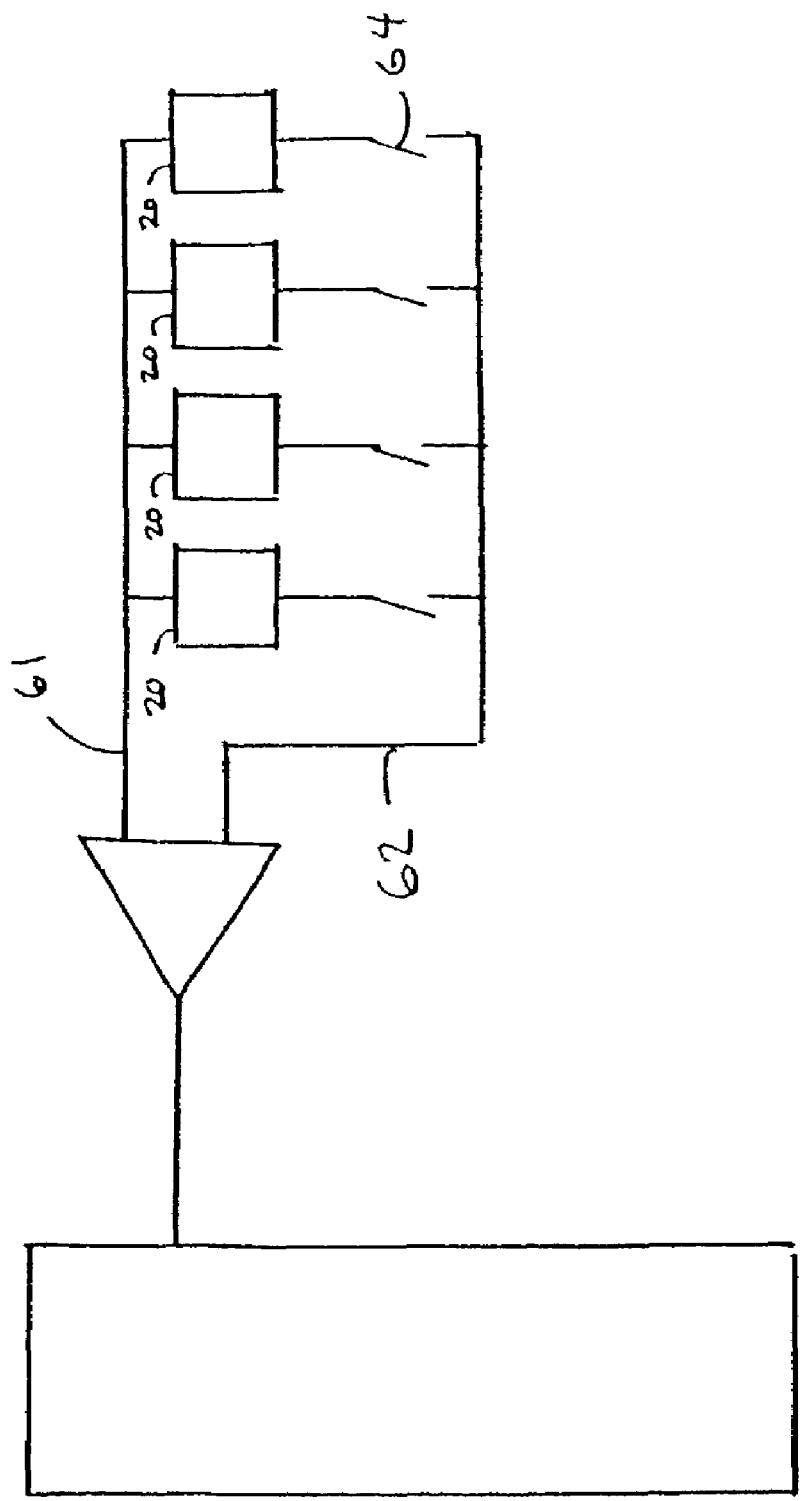
FIG. 8 is a wiring diagram for connecting a plurality of temperature sensors with a common wire.

The temperature sensors 20 can be electrically connected as illustrated in FIG. 8. Each temperature sensor 20 can be coupled with a common wire 61 and then include its own return wire 62. Accordingly, N+1 wires can be used to independently sense the temperature at the temperature sensors 20 when N temperature sensors 20 are employed. The temperature at a particular temperature sensor 20 can be determined by closing a switch 64 to complete a circuit between the temperature sensor's 20 return wire 62 and the common wire 61. When the temperature sensors 20 are thermocouples, the temperature can be calculated from the voltage in the circuit using, for example, a sensing circuit 63. To improve the flexibility of the sheath 16, the individual return wires 62 can have diameters which are smaller than the common wire 61 diameter.

Each temperature sensor 20 can also be independently wired. Employing N independently wired temperature sensors 20 requires 2N wires to pass the length of the sheath 16.

The sheath 16 or inner core 34 flexibility can also be improved by using fiber optic based temperature sensors 20. The flexibility can be improved because only N fiber optics need to be employed sense the temperature at N temperature sensors 20.

Figure 9:
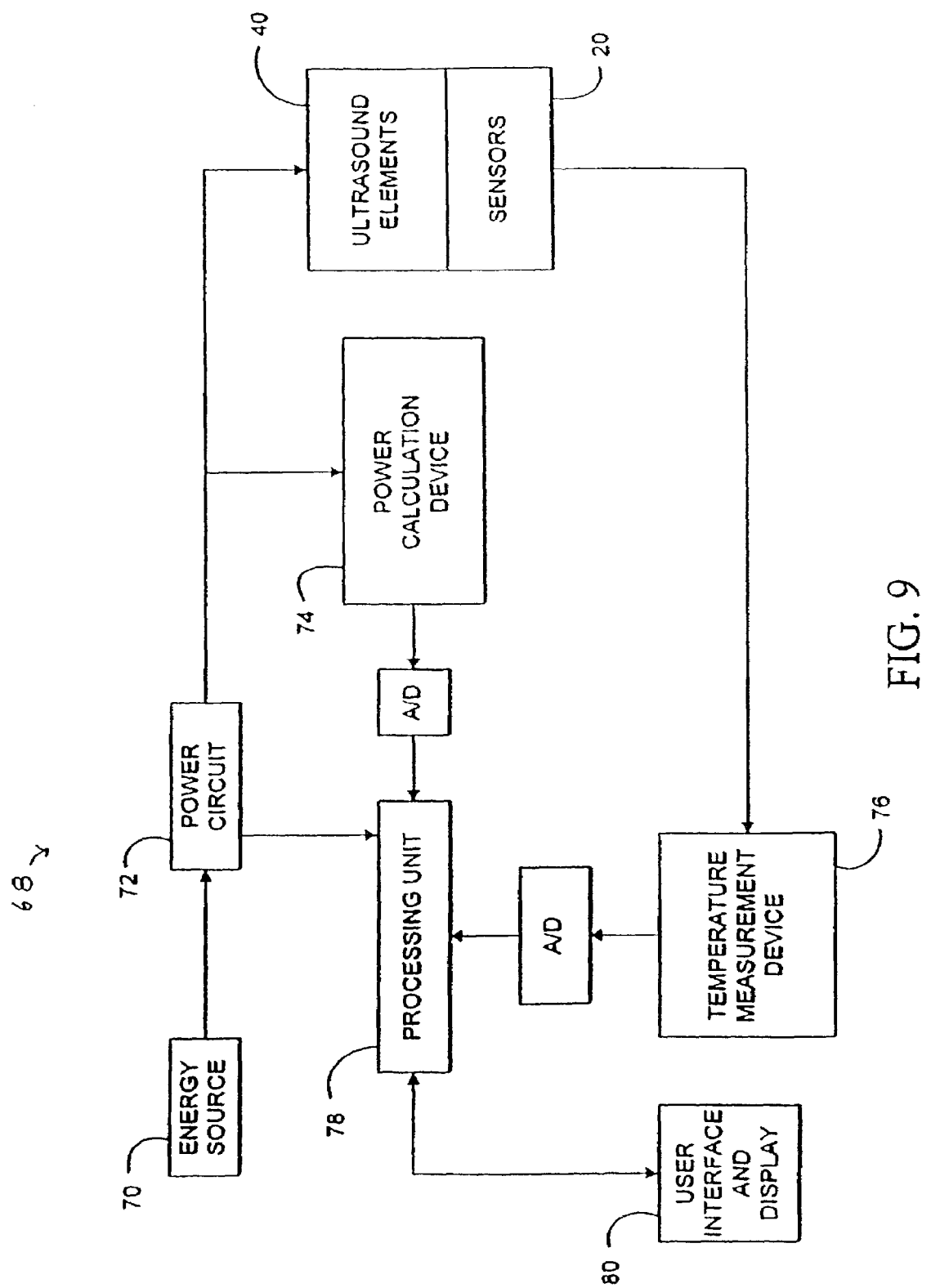
FIG. 9 is a block diagram of a feedback control system for use with the ultrasonic catheter

The catheter 10 can be used a feedback control system 68 as illustrated in FIG. 9. The temperature at each temperature sensor 20 is monitored and the output power of energy source adjusted accordingly. The physician can, if desired, override the closed or open loop system.

The feedback control system 68 includes an energy source 70, power circuits 72 and a power calculation device 74 coupled with the ultrasound radiating members 40. A temperature measurement device 76 is coupled with the temperature sensors 20 on the sheath 16 or inner core 34. A processing unit 78 is coupled with the power calculation device 74, the power circuits 72 and a user interface and display 80.

In operation, the temperature at each temperature sensor 20 is determined at the temperature measurement device 76. The processing unit 78 receives each determined temperature from the temperature measurement device 76. The determined temperature can then be displayed to the user at the user interface and display 80.

The processing unit 78 includes logic for generating a temperature control signal. The temperature control signal is proportional to the difference between the measured temperature and a desired temperature. The desired temperature can be determined by the user or be preset within the processing unit 78. The user can set the predetermined temperature at the user interface and display 80.

The temperature control signal is received by the power circuits 72. The power circuits 72 can be configured to adjust the power level, voltage, phase and/or current of the energy supplied to the ultrasound radiating members 40 from the energy source 70. For instance, when the temperature control signal is above a particular level, the power supplied to a particular ultrasound radiating member 40 can be reduced in response to the temperature control signal. Similarly, when the temperature control signal is below a particular level, the power supplied to a particular ultrasound radiating member 40 can be adjusted in response to the magnitude of the temperature control signal. After each power adjustment, the processing unit 78 monitors the temperature sensors 20 and produces another temperature control signal which is received by the power circuits 72.

The processing unit 78 can also include safety control logic. The safety control logic detects when the temperature at a temperature sensor 20 has exceeded a safety threshold. The processing unit 78 can then provide a temperature control signal which causes the power circuits 72 to reduce or stop the delivery of energy from the energy source 70 to the ultrasound radiating members 40.

Because the ultrasound radiating members 40 may be mobile relative to the temperature sensors 20, it can be unclear which ultrasonic transducer should have a power, voltage, phase or current level adjustment. As a result, each member may be identically adjusted. In a modified arrangement, the power, voltage, phase, and current supplied to each of the ultrasound radiating members 40 may be adjusted in response to the temperature sensor 20 which indicates the highest temperature. Making voltage, phase and/or current adjustments in response to the temperature of the temperature sensor 20 indicating the highest temperature can prevent overheating of the treatment site.

The processing unit 78 also receives a power signal from a power calculation device 74. The power signal can be used to determine the power being received by each ultrasound radiating member 40. The determined power can then be displayed to the user on the user interface and display 80.

The feedback control system 68 can maintain the tissue adjacent to the ultrasound radiating members 40 below a desired temperature. For example, it is generally desirable to prevent the tissue adjacent to the ultrasound radiating member 40 from increasing more than 6 degrees Celsius above body temperature. As described above, the ultrasound radiating members 40 can be electrically connected so each ultrasound radiating member 40 can generate an independent output. The output maintains a selected energy at each ultrasound radiating member 40 for a selected length of time.

The processing unit 78 can be a digital or analog controller, or a computer with software. When the processing unit 78 is a computer it can include a CPU coupled through a system bus. The user interface and display 80 can be a mouse, keyboard, a disk drive, or other non-volatile memory systems, a display monitor, and other peripherals, as are known in the art. Also coupled to the bus is a program memory and a data memory.

In lieu of the series of power adjustments described above, a profile of the power delivered to each ultrasound radiating member 40 can be incorporated in the processing unit 78 and a preset amount of energy to be delivered may also be profiled. The power delivered to each ultrasound radiating member 40 can the be adjusted according to the profiles.

Figure 10A:
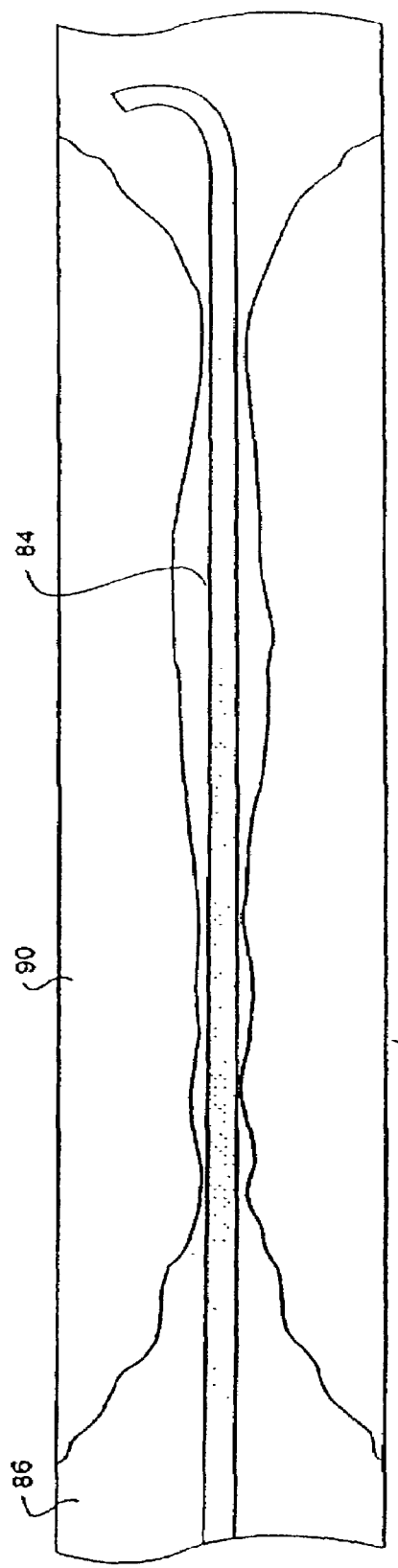
FIG. 10A is a cross-sectional view of a treatment site.

FIGS. 10A–10G illustrate a method for using the ultrasonic catheter 10. In FIG. 10A, a guidewire 84 similar to a guidewire used in typical angioplasty procedures is directed through vessels 86 toward a treatment site 88 which includes a clot 90. The guidewire 84 is directed through the clot 90. Suitable vessels include, but are not limited to, the large periphery blood vessels of the body. Of course, as mentioned above, the ultrasonic catheter 10 may also find utility various imaging applications or for treating and/or diagnosing other diseases in other body parts.

Figure 10B:
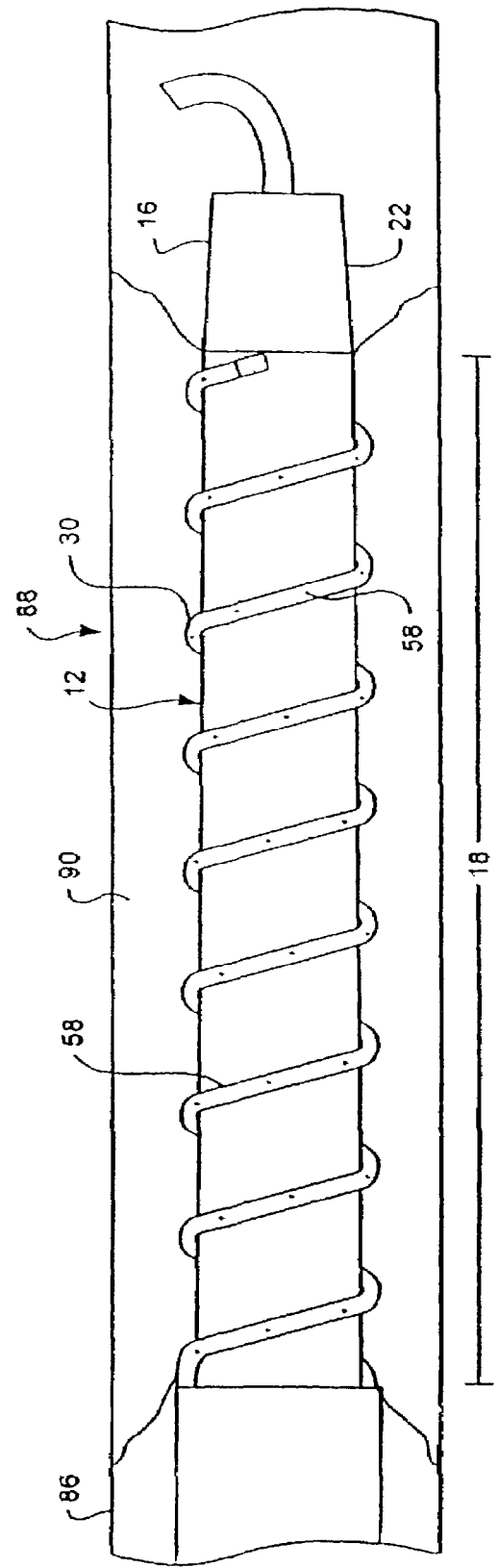
FIG. 10B is a side view of the distal end of an ultrasonic catheter positioned at the treatment site.

In FIG. 10B, the utility lumen 28 of the sheath 16 is slid over the guidewire 84 and the sheath 16 is advanced along the guidewire 84 using traditional over-the-guidewire techniques. The sheath 16 is advanced until the energy delivery section 18 of the sheath 16 is positioned at the clot 90. Radiopaque markers may be positioned at the energy delivery section 18 of the sheath 16 to aid in the positioning of the sheath 16 within the treatment site 88.

Figure 10C:
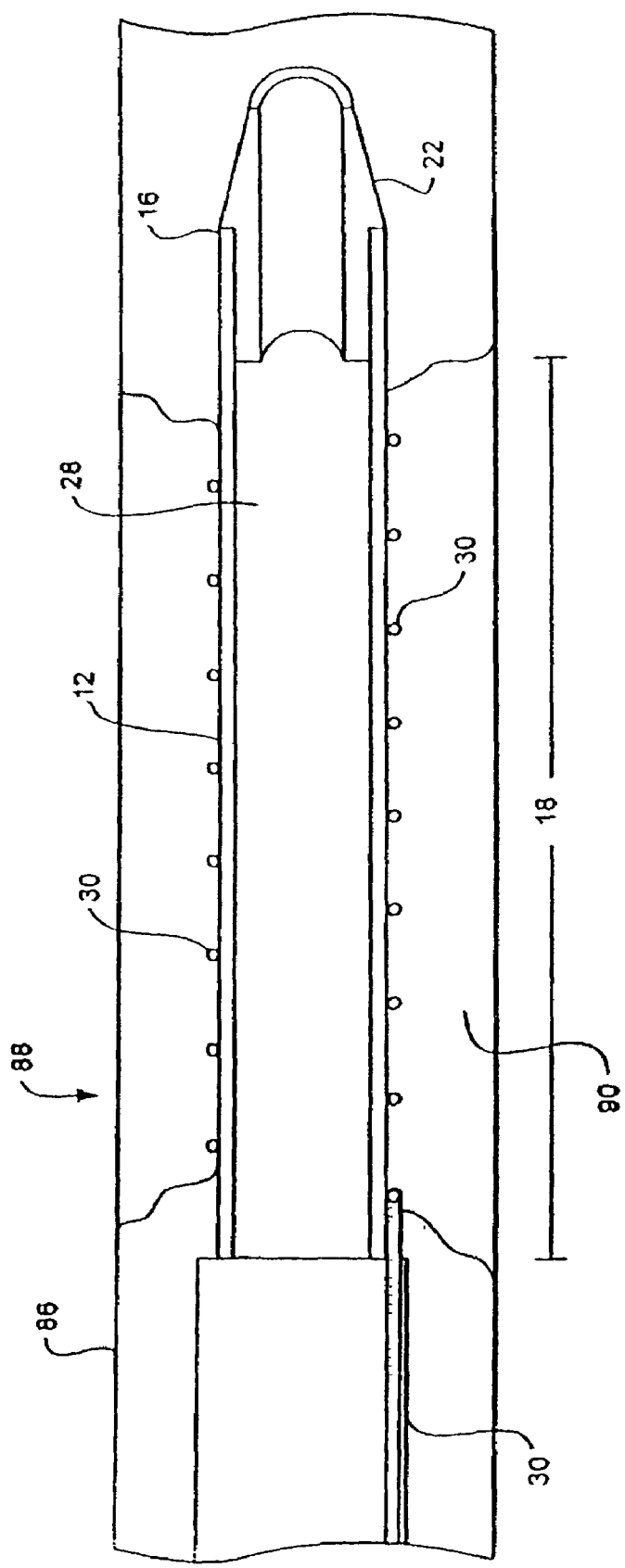
FIG. 10C is a cross-sectional view of the distal end of the ultrasonic catheter of FIG. 10B positioned at the treatment site.

In FIG. 10C, the guidewire 84 is withdrawn from the utility lumen 28 by pulling the guidewire 84 proximally while holding the sheath 16 stationary. In FIG. 10D, a temperature monitor 92 is coupled with the temperature sensor leads 24, a cooling fluid source 94 is coupled with the cooling fluid inlet 46 and a drug solution source 96 is coupled with the drug inlet port 32. The drug solution source 96 can be a syringe with a Luer fitting which is complementary with the drug inlet port 32. Pressure can be applied to a plunger 98 on the drug solution source 96 to drive the drug solution through the drug delivery lumen 56. The drug solution is delivered from the drug delivery lumen 56 through the drug delivery ports 58 as illustrated by the arrows 100 in FIG. 10E. Suitable drug solutions include, but are not limited to, an aqueous solution containing genetic material including both DNA and RNA, oligonucleotides, polynucleotides which contain nucleic acid analogs, Heparin, Uronkinase, Streptokinase, or Tissue Plasminogen Activator (TPA).

In FIG. 10F, the inner core 34 is inserted into the utility lumen 28 until the ultrasound radiating member 40 is positioned within the energy delivery section 18. To aid in placement of the ultrasound radiating member 40 within the energy delivery section 18, radiopaque markers may be positioned on the inner core 34 adjacent to each of the ultrasound radiating members 40 or the ultrasound radiating members 40 themselves can be radiopaque. In other embodiments, the ultrasound energy radiated by the ultrasound radiating members can be used to aid placement. Once the inner core 34 is properly positioned, the ultrasound radiating member 40 is activated to deliver ultrasound energy through the energy delivery section 18 to the clot 90. Suitable ultrasound energy is delivered with a frequency from about 20 KHz to 20 MHz. In one embodiment, the ultrasound energy is about 500 KHz to 20 MHz. In another embodiment, the ultrasound energy is about 1 MHz and 3 MHz. In yet another embodiment, the sound waves have a frequency of about 3 MHz. While the ultrasound energy is being delivered, the ultrasound radiating member 40 can be moved within the energy delivery section 18 as illustrated by the arrows 52. The movement of the ultrasound radiating member 40 within the energy delivery section 18 can be caused by manipulating the proximal end 36 of the inner core 34 while holding the back end hub 33 stationary. In the illustrated embodiment, a cooling fluid flows through the cooling fluid lumen 44 and out the occlusion device 22.

The cooling fluid can be delivered before, after, during or intermittently with the delivery of the ultrasound energy. Similarly, the drug solution can be delivered before, after, during or intermittently to the delivery of ultrasound energy. As a result, the acts illustrated in FIGS. 10A–10F can be performed in different orders than are described above. The drug solution and energy are applied until the clot 90 is partially or entirely dissolved as illustrated in FIG. 10G. Once the clot 90 has been dissolved to the desired degree, the sheath 16 and inner core 34 are withdrawn from the treatment site 88.

Figure 11A:
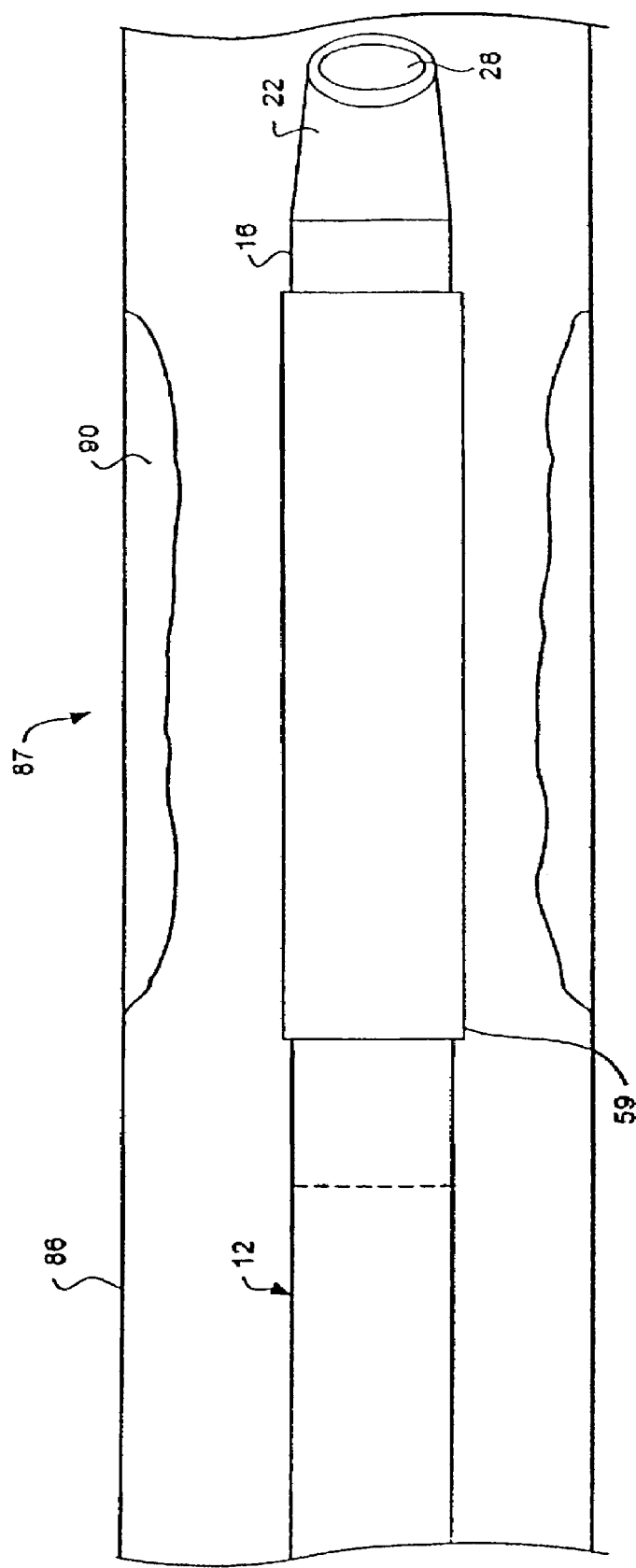
FIG. 11A illustrates an ultrasonic catheter with a balloon device positioned at the treatment site.
Figure 11B:
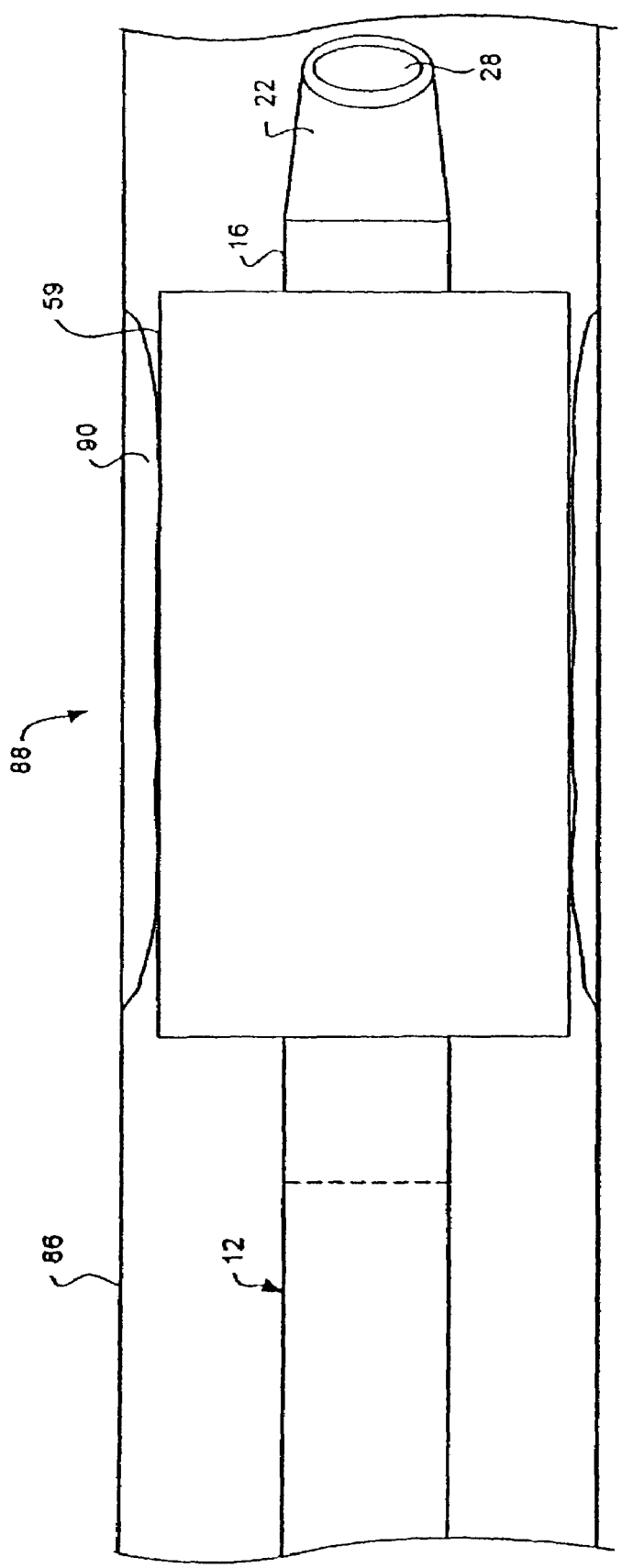
FIG. 11B illustrates an ultrasonic catheter with a deployed balloon device positioned at the treatment site.

FIGS. 11A–11B illustrate a method for using the system 10 when the sheath distal end 15 includes a balloon device 59. The catheter 10 is advanced through a vessel 86, as described above, until the balloon device 59 is positioned adjacent a treatment site as illustrated in FIG. 11A. The balloon device 59 is expanded until the balloon device 59 contacts the clot 90 as illustrated in FIG. 11B. As described above, the balloon device 59 can be expanded by delivering a drug solution through an expansion port 60A or a drug delivery port 58 or by delivering an expansion media through an expansion port 60A. Once the balloon device 59 contacts the clot 90, the drug solution or components of the drug solution are driven across the membrane so the drug solution or the components of the drug solution contact the clot 90. The inner core 34 can be inserted into the sheath 16 before, after or concurrently with the expansion of the balloon 59 and/or the delivery of the drug solution. Similarly, the ultrasound radiating member 40 can be operated before, after, intermittently or concurrently with the expansion of the balloon device 59 and/or the delivery of the drug solution.

II. Overview of a Small Vessel Ultrasonic Catheter

Figure 12:
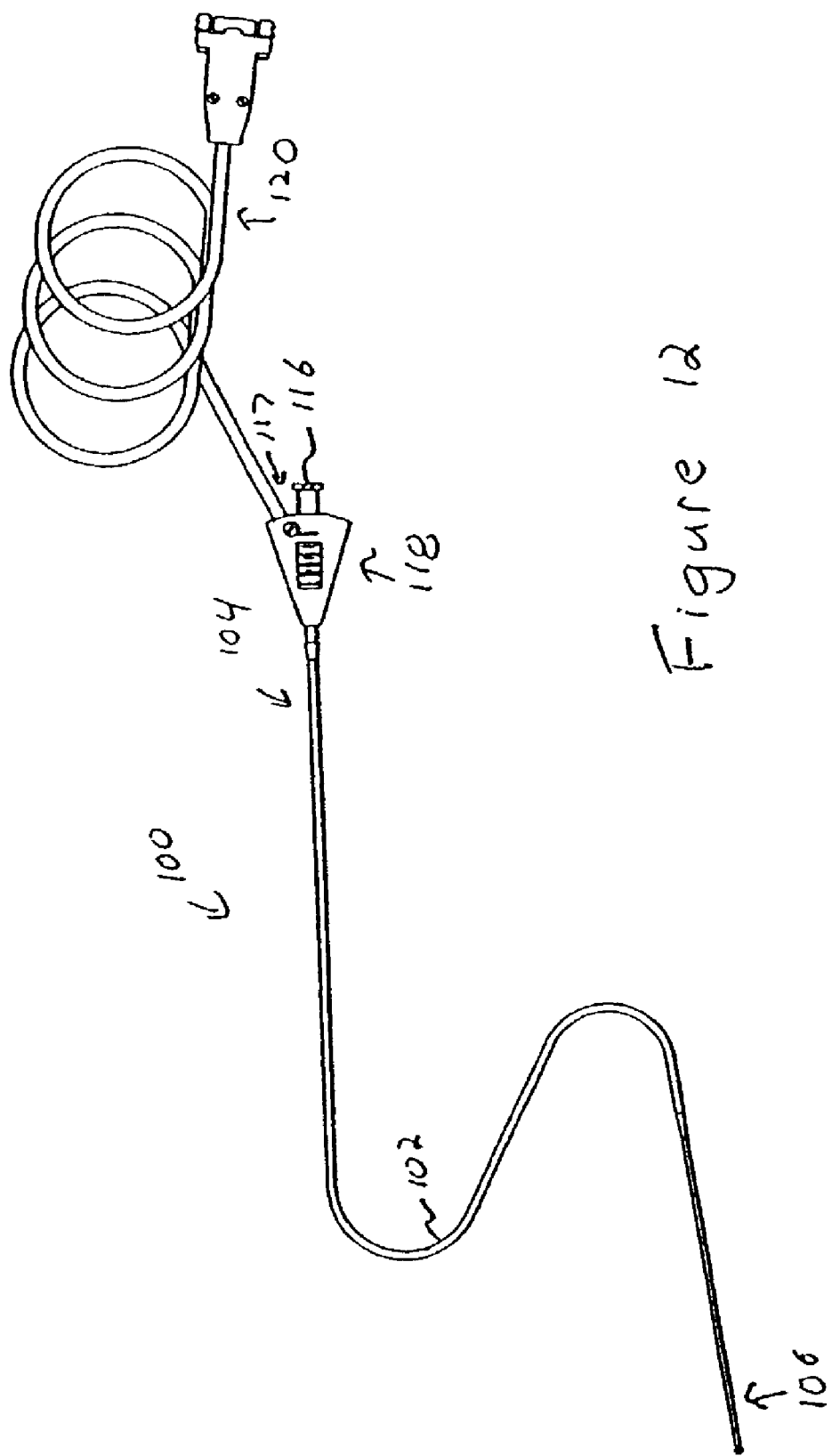
FIG. 12 is a side view of an ultrasonic catheter that is particularly configured for insertion into small vessels of the human body.
Figure 13:
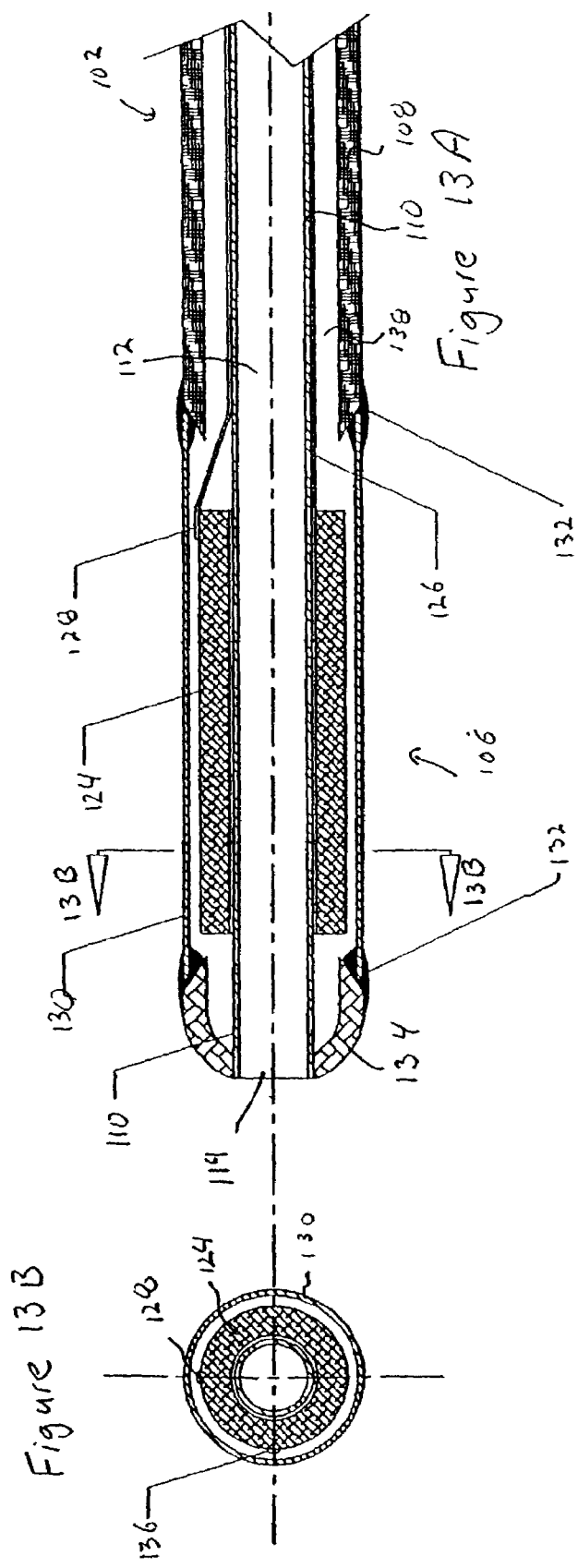
FIG. 13A is a cross-sectional view of a distal end of the ultrasonic catheter of FIG. 12.
FIG. 13B is a cross-sectional view of the ultrasonic catheter taken through line 13B—13B of FIG. 13A.

FIGS. 12–13B illustrate another embodiment of an ultrasonic catheter 100. This embodiment is particularly suited for use with small vessels of the distal anatomy, such as, for example, the small neurovascular vessels in the brain.

As shown in FIGS. 12 and 13A, the ultrasonic catheter 100 generally comprises a multi-component tubular body 102 having a proximal end 104 and a distal end 106. As with the long segment catheter described above, the tubular body 102 and other components of the catheter 100 can be manufactured in accordance with any of a variety of techniques well know in the catheter manufacturing field. Suitable material dimensions can be readily selected taking into account the natural and anatomical dimensions of the treatment site and of the desired percutaneous access site.

The elongate flexible tubular body 102 comprises an outer sheath 108 (see FIG. 13A) that is positioned upon an inner core 110. In one embodiment particularly suited for small neurovascular vessels, the outer sheath 108 comprises extruded PTFE, PEEK, PE, polymides, braided polymides and/or other similar materials, having an outside diameter of approximately 0.039 inches at the proximal end and approximately 0.033–0.039 inches at the distal end. In such an embodiment, the outer sheath 108 has an axial length of approximately 150 centimeters. In other embodiments, the outer sheath 108 can be formed from a braided tubing formed of, by way of example, to high or low density polyethylenes, urethanes, nylons, etc. Such an embodiment enhances the flexibility of the tubular body 102. In such an embodiment, the outer sheath 108 can include a stiffening member at the proximal end of the tubular body 102.

The inner core 110 defines, at least in part, a central guide wire lumen 112, which preferably extends through the length of the catheter 100. The central lumen 112 has a distal exit port 114 and a proximal axis port 116. As best seen in FIG. 12, the proximal access port 116 is defined by drug inlet port 117 of a back end hub 118, which is attached to the proximal end 104 of the other sheath 108. The illustrated back end hub 118 is preferably attached to a control box connector 120, the utility of which will be described below.

The central lumen 112 is preferably configured to receive a guide wire (not shown). In one embodiment, the guide wire has a diameter of approximately 0.010 to 0.012 inches. The inner core 110 is preferably formed from polymide or a similar material, which is some embodiments can be braided to increase the flexibility of the tubular body 102.

With particular reference to FIGS. 13A and 13B, the distal end 106 of the catheter 102 preferably includes an ultrasound radiating member 124. In the illustrated embodiment, the ultrasound radiating member 124 comprises an ultrasonic transducer, which converts, for example, electrical energy into ultrasonic energy. In a modified embodiment, the ultrasound energy can be generated by an ultrasonic transducer that is remote from the ultrasound radiating member 40 and the ultrasonic energy can be transmitted via, for example, a wire to the ultrasound radiating member 40.

In the illustrated embodiment, the ultrasound radiating member 124 is in the shape of a hollow cylinder. As such, the central core 110 can extend through the ultrasound radiating member 124, which is positioned over the central core 110. The ultrasound radiating member 124 can be secured to the central core in any suitable manner, such as with an adhesive. In other embodiments, the ultrasound radiating member 124 can be of a different shape, such as, for example, a solid rod, a disk, a solid rectangle or a thin block attached to the central core 110. The ultrasound radiating member 124 can also be formed from a plurality of smaller ultrasound radiating members. The illustrated arrangement is generally preferred because it provides for enhanced cooling of the ultrasound radiating member 124.

Specifically, as will be explained in more detail below, a drug solution can be injected through the central lumen 112 thereby providing a heat sink for any heat generated by the ultrasound radiating member 124.

As mentioned above, suitable frequencies for the ultrasound radiating member 40 include, but are not limited to, from about 20 KHz and less than about 20 MHz. In one embodiment, the frequency is between about 500 KHz and 20 MHz and in another embodiment between about 1 MHz and 3 MHz. In yet another embodiment, the sound waves have a frequency of about 3 MHz.

As mentioned above, in the illustrated embodiment, ultrasonic energy is generated from electrical power supplied to the ultrasound radiating member 124. The electrical power can be supplied through the controller box connector 120, which is connected to a pair wires 126, 128 that extend through the catheter body 102. The electrical wires 126, 128 can be secured to the inner core 110, lay along the inner core 110 and/or extend freely in the space between the inner core 110 and the outer sheath 108. In the illustrated arrangement, the first wire 126 is connected to the hollow center of the ultrasound radiating member 124 while the second wire 128 is connected to the outer periphery of the ultrasound radiating member 124. The ultrasound radiating member 124 is preferably formed from, but is not limited to, a piezolectic ceramic oscillator or a similar material.

With continued reference to FIGS. 13A and 13B, the distal end 104 of the catheter 100 preferably includes sleeve 130, which is generally positioned about the ultrasound radiating member 124. The sleeve 130 is preferably constructed from a material which readily transmits ultrasound energy. Suitable materials for the energy delivery section 18 include, but are not limited to, polyolefins, polyimides, polyester and other low ultrasound impedance materials. Low ultrasound impedance materials are materials which readily transmit ultrasound energy with minimal absorption of the ultrasound energy. The proximal end of the sleeve 130 can attached to the outer sheath 108 with an adhesive 132. In a similar manner, the distal end of the sleeve 130 can be attached to a tip 134 of the catheter 100. In the illustrated arrangement, the tip 134 is generally rounded and is also attached to the distal end of the inner core 110.

Preferably, the tubular body 102 can be divided into at least three sections of varying stiffness. The first section, which preferably includes the proximal end 104, is generally more stiff than a second section, which lies between the proximal end 104 and the distal end 106 of the catheter. This arrangement facilitates the movement and placement of the catheter 102 within small vessels. The third section, which includes ultrasound radiating element 124, is generally stiffer than the second section. The third section is generally stiffer than the second section due to the presence of the ultrasound radiating element 124.

With continued reference to FIG. 13B, the catheter 100 preferably includes at least one temperature sensor 136 that is located at the distal end 106 of the catheter 100 near the ultrasound radiating member 124. Suitable temperature sensors include but are not limited to, diodes, thermistors, thermocouples, resistance temperature detectors (RTDs), and fiber optic temperature sensors that used thermalchromic liquid crystals. As with the long segment catheter described above, the temperature sensors preferably operatively connected to a control box (not shown) through a control wire, which extend through the catheter body 102 and back end hub 118 and is operatively connected to a control box through the control box connector 120. The control box preferably includes a feedback control system, such as the control system described above. As with the long segment embodiment, the control box is preferably configured to monitor and control the power, voltage, current and phase supplied to the ultrasound radiating members. In this manner, temperature of the catheter can be monitored and controlled.

In use, a free end of a guidewire is percutaneously inserted into the arterial system at a suitable first puncture site. The guidewire is advanced through the vessels towards a treatment site, which includes a clot. The guidewire wire is preferably then directed through the clot.

The catheter 100 is thereafter percutaneously inserted into the first puncture site and advanced along the guidewire towards the treatment site using traditional over-the-guidewire techniques. The catheter 100 is advanced until the distal end 106 of the catheter 100 is positioned at or within the clot. The distal end 106 can includes radio opaque markers to aid positioning the distal end 106 within the treatment site.

The guidewire can then be withdrawn from the central lumen 112. A drug solution source (not shown), such as a syringe with a Luer fitting, is attached to the drug inlet port 117 and the controller box connector 120 is connected to the control box. As such, the drug can be delivered to the distal access port 114 to the clot through the central lumen 112. As with the long segment catheter, suitable drug solutions for treating thrombus include, but are not limited to, an aqueous solution containing Heparin, Uronkinase, Streptokinase, and/or tissue Plasminogen Activator (TPA).

The ultrasound radiating member 124 is activated to deliver ultrasonic energy through the distal end 106 of the catheter 100 to the clot. As mentioned above, suitable frequencies for the ultrasound radiating member 40 include, but are not limited to, from about 20 KHz and less than about 20 MHz. In one embodiment, the frequency is between about 500 KHz and 20 MHz and in another embodiment between about 1 MHz and 3 MHz. In yet another embodiment, the sound waves have a frequency of about 3 MHz. The drug solution and ultrasonic energy are applied until the clot is partially or entirely dissolved. Once the clot has been dissolved to the desired degree, the catheter 100 can be withdrawn from the treatment site.

In the modified arrangement, the catheter 100 can be provided with a cooling system for removing heat generated by the ultrasound radiating member 124. In one embodiment, a return path can be formed in the space 138 such that coolant from a coolant system can be directed through the space 138 (see FIG. 13A).

III. Alternate Site Gene Therapy

A preferred embodiment of the present invention relates to the use of ultrasound to assist the entry of a gene therapy agent into a cell in a selected section of a body lumen in order to transform the cell and express a gene product encoded by the gene therapy agent in the cell. In some embodiments the gene therapy agent is taken up by one or more cells in a selected section of a body lumen in order to transform one or more cells and express a gene product encoded by the gene therapy agent in one or more cells. In one particular embodiment, the selected section of the body lumen is in a diseased or injured state. For example, the selected section of the body lumen may be a section of the body lumen which is suffering from atherosclerosis or has undergone restenosis. In another particular embodiment, the selected section of the body lumen has been injured by the performance of a medical procedure adjacent the section.

Balloon angioplasty and rotational atherectomy are two examples of medical procedures which are known to cause injuries to a section of a body lumen.

According to a preferred embodiment of the present invention, the rate at which a gene therapy agent is absorbed into cells in the selected section of the body lumen is accelerated by the application of ultrasound to the selected section. In some instances, entry of the gene therapy agent is made possible by the application of ultrasound. It is believed that accelerated absorption of the gene therapy agent is due to cavitation of the cell membrane.

Also according to a preferred embodiment of the present invention, ultrasound is believed to facilitate the passage of a gene therapy agent between cells so that the gene therapy agent may be absorbed by cells which are not at the surface of the body lumen. Accordingly, a feature of the present invention is the use of ultrasound to assist the entry of a gene therapy agent into cells which are not at a surface of a body lumen in order to transform the cell and express a gene product encoded by the gene therapy agent in the cell.

In one preferred embodiment of the present invention, the catheter includes: a distal catheter body including an expandable member for occluding the selected section of the body lumen; a gene therapy composition delivery lumen connected to one or more gene therapy composition delivery ports in the distal catheter body for delivering a gene therapy composition to the selected section of the body lumen through the expandable member, the gene therapy composition delivery lumen containing a gene therapy agent; and an ultrasound element for delivering ultrasound energy to the selected section of the body lumen. According to this embodiment, types of expandable members that may be used include, but are not limited to a porous balloon, a microporous balloon, a macroporous balloon, a balloon within a balloon, a channeled balloon, an infusion sleeve, a hydrogel balloon, an iontophoretic balloon, or a coated stent on the outside of a balloon. Examples of these types of expandable members are described in Eur Heart J., 16 437–440 (1995) which is incorporated herein by reference.

A catheter is used to deliver the gene therapy agent to a selected section of a body lumen. In general, any catheter may be used which includes a mechanism for delivering a gene therapy composition to a selected section of the body lumen; and a mechanism for delivering ultrasound energy to the isolated section of the body lumen. It is preferred that the mechanism for delivering the gene therapy composition to the selected section of the body lumen be designed so that it maintains the gene therapy composition at or adjacent to the selected section in a relatively high, undiluted concentration, for example, at or near the concentration that the gene therapy composition was delivered.

The catheter can be used in various body lumens including, but not limited to, the blood vessels, pancreas, sinuses, esophagus, rectum, vessels adjacent the prostate, vessels in or adjacent to the brain, gastrointestinal vessels and urological vessels. The catheter is selected from a variety of different sizes, diameter and length, depending on the type and location of the lesion.

Figure 14:
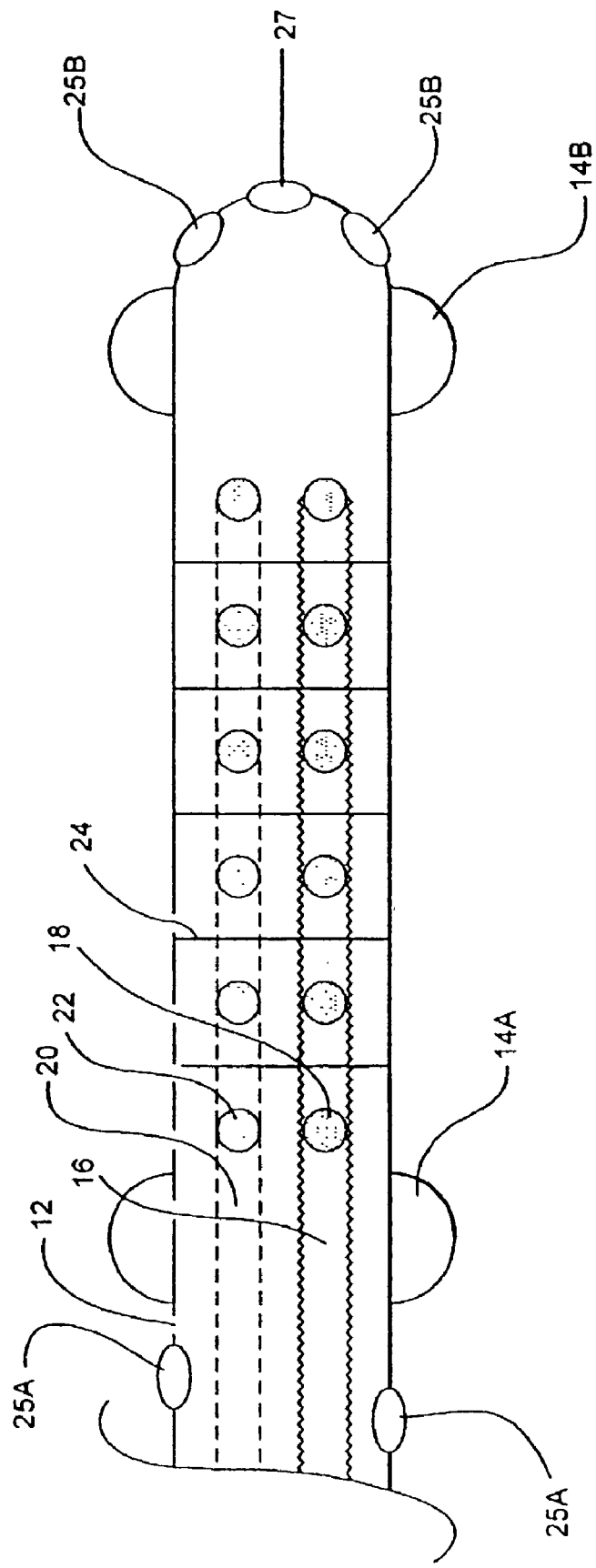
FIG. 14 illustrates a catheter with proximal and distal expandable members may be used in the present invention.

FIG. 14 illustrates an embodiment of a catheter which may be used in the present invention. As illustrated, the catheter includes a distal catheter body 12 with proximal and distal expandable members 14A, 14B for occluding sections of a body lumen proximal and distal to a selected section of the body lumen. The catheter also includes a gene therapy composition delivery lumen 16 which terminates in one or more gene therapy composition delivery ports 18 at the distal catheter body 12. The gene therapy composition delivery ports 18 are preferably positioned relative to the one or more expandable members 14A, 14B such that a gene therapy composition is delivered into the body lumen between the proximal and distal occluded sections of the body lumen.

The catheter also includes a wash lumen 20 which terminates in one or more washing ports 22 at the distal catheter body 12. The washing ports 22 are preferably positioned relative to the one or more expandable members 14A, 14B such that a washing fluid, such as saline or a microbubble booster, may be delivered into the body lumen between the proximal and distal occluded sections of the body lumen. The washing fluid can be used to wash the selected section of the body lumen prior to delivery of the gene therapy composition, for example to remove blood from the selected section. The washing fluid can also be used to wash the selected section of the body lumen after delivery of the gene therapy composition in order to remove non-absorbed gene therapy composition from the selected section of the body lumen. Ultrasound energy is optionally delivered during the washing step(s). Although not shown, the catheter can also include a bypass lumen to allow fluid to pass through the lumen while the lumen is occluded that would otherwise pass through the lumen. Further details of preferred embodiments of catheters used in the present invention are described in U.S. Pat. No. 6,135,976, titled METHOD, DEVICE AND KIT FOR PERFORMING GENE THERAPY, issued Oct. 24, 2000.

Figure 15:
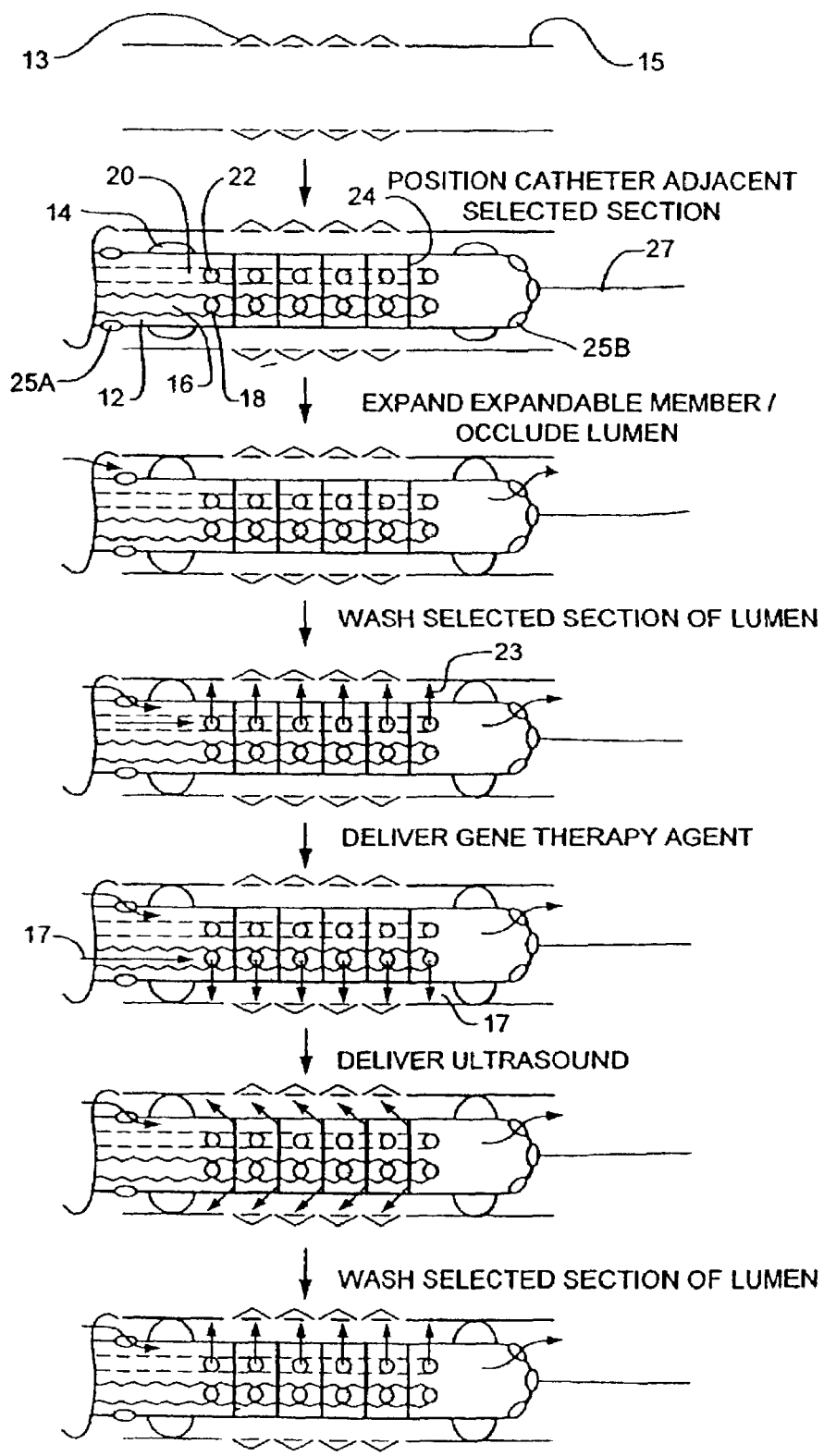
FIG. 15 illustrates a method of gene therapy using the catheter illustrated in FIG. 14.

FIG. 15 illustrates a particular embodiment of the method for performing gene therapy on a selected section of a body lumen which utilizes a catheter such as the one illustrated in FIG. 14. According to the method, a distal catheter body 12 is placed in a selected section 13 of a body lumen 15 such that expandable members 14A, 14B on the catheter are proximal and distal to the selected section 13 of the body lumen 15. The expandable members 14A, 14B are expanded in order to occlude the body lumen 15. A gene therapy composition 17 is then delivered into the selected section 13 of the body lumen 15. Ultrasound energy 19 is then delivered for a period of time, the ultrasound facilitating the entry of gene therapy agents in the composition to enter into the cells. As illustrated in FIG. 15, the method may optionally also include the step of washing the selected section 13 of the body lumen 15, for example by delivering and removing saline 23, prior to delivering the gene therapy composition 17. The method may also optionally include the step of washing the selected section 13 of the body lumen 15, for example by delivering and removing saline 23, after delivering the gene therapy composition 17, This prevents the gene therapy agent from transfecting cells outside the region. Ultrasound energy may be delivered during one or both of the washing steps, optionally in the presence of a microbubble booster. It is believed that the use of ultrasound energy during the washing step prior to delivery of the gene therapy composition pretreats the body lumen for the entry of the gene therapy composition into cells of the body lumen. Further details of preferred embodiments of methods for performing gene therapy on a selected section of a body lumen are described in U.S. Pat. No. 6,135,976, titled METHOD, DEVICE AND KIT FOR PERFORMING GENE THERAPY, issued Oct. 24, 2000.

Two areas of the body where injured or diseased regions of the body lumen are often found are near the heart or the brain. The proper function and vascularization of these organs are critical to sustain life in human beings and many other organisms. Occluding the vessels, and thus blocking the flow of oxygen and other nutrients to, as well as the removal of waste products from, these life-sustaining organs, such as the heart or brain (just to name two of many such organs), even for a short period of time, would likely be dehabilitating or fatal for the patient. There are at least two explanations for this. First, organs such as the heart and brain rely heavily on aerobic metabolism to sustain itself and become ischemic in the absence of oxygen. In contrast to skeletal muscles, the heart and brain cannot rely on anaerobic metabolism to sustain itself. Second, relative to a highly vascularized region of the human anatomy, such as the legs, the heart and brain have fewer vessels or pathways for oxygen and nutrients to reach them. The result of this is that any degree of occlusion can drastically reduce the blood flow to these organs. In contrast, there are many vessels in the leg, so there are many more shunts or alternative routes for the bloodflow to reach its target.

One possible approach to sustaining bloodflow to a target site, such as the heart or brain, while occluding injured or diseased segment of the body lumen is to utilize a bypass lumen, such as the one described by U.S. Pat. No. 6,135,976, titled METHOD, DEVICE AND KIT FOR PERFORMING GENE THERAPY, issued Oct. 24, 2000. However, even this approach has the risk of not providing adequate bloodflow to target sites.

A preferred embodiment of the present invention greatly reduces the risk of inadequate blood supply to critical organs by performing gene therapy on a segment of the body lumen at an alternate site (hereinafter "treatment segment"). The alternate site preferably is one that has a high degree of vascularization relative to the target sites. The alternate site is also preferably one that is able to resort to anaerobic metabolism when there is decreased flow of oxygenated blood to the target site. One example of an alternate site for performing gene therapy on a treatment segment are the blood vessels running to the skeletal muscles in the leg. These vessels are highly vascularized, providing many routes to the target skeletal muscle. In addition, skeletal muscle has the benefit of utilizing anaerobic as well as aerobic metabolism, so it can sustain itself even when its blood supply is temporary blocked off.

In one preferred embodiment of the present invention, the entry of gene therapy agents into the cells of the treatment segment transform these cells so that they express a gene product encoded by the gene therapy agents, and thereby become healthy versions of the cells found at the injured or diseased segment portion of the body lumen. In another preferred embodiment of the present invention, the entry of gene therapy agents into the cells of the treatment segment initiates or facilitates the generation of new cells that are healthy versions of the cells found at the injured or diseased segment portion of the body lumen.

According to a preferred embodiment of the present invention, the treatment segment with the newly formed healthy cells are then transplanted into the region of body lumen that is injured of diseased. The transplanted treatment segment replaces the injured or diseased segment of the body lumen.

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

What is claimed is:

1. A method for performing gene therapy on a selected section of a body lumen comprising:
   placing within a selected section of the body lumen a catheter including one or more expandable members for occluding sections of the body lumen proximal and/or distal to the selected section;
   occluding sections of the body lumen proximal and/or distal to the selected section of the body lumen;
   delivering a gene therapy composition into the selected section of the body lumen;
   delivering ultrasound to the selected section of the body lumen for a period of time in the presence of the gene therapy composition under conditions where the ultrasound causes cavitation of cells in the selected section; and
   after delivering the gene therapy composition and ultrasound to the selected section of the body lumen, transplanting the selected section of the body lumen into another region of the body.

2. The method according to claim 1 wherein said selected section of the body lumen is highly vascularized.

3. The method according to claim 1 wherein said selected section of the body lumen is capable of anaerobic metabolism.

4. The method according to claim 1 wherein said selected section of the body lumen is highly vascularized and capable of anaerobic metabolism.

5. The method of claim 1, wherein the selected section of the body lumen is a blood vessel of leg skeletal muscle.

6. The method of claim 1, wherein the gene therapy composition comprises a gene operably linked to a promoter for expression in one or more cells within the selected section of the body lumen.

7. The method of claim 6, wherein the gene produces a gene product which reduces the immune response to grafts.

8. The method of claim 6, wherein the gene produces a gene product which blocks cell proliferation.

9. The method of claim 1, wherein the gene therapy composition comprises an oligonucleotide.

* * * * *